(12) United States Patent
An et al.

(10) Patent No.: US 11,795,215 B2
(45) Date of Patent: Oct. 24, 2023

(54) ANTI-MESOTHELIN CHIMERIC ANTIGEN RECEPTOR SPECIFICALLY BINDING TO MESOTHELIN

(71) Applicant: CELLENGENE INC, Seoul (KR)

(72) Inventors: Jae Hyung An, Seoul (KR); Na Kyung Han, Seoul (KR)

(73) Assignee: CELLENGENE INC, Seoul (KR)

( * ) Notice: Subject to any disclaimer, the term of this patent is extended or adjusted under 35 U.S.C. 154(b) by 0 days.

(21) Appl. No.: 17/602,328

(22) PCT Filed: Apr. 30, 2021

(86) PCT No.: PCT/KR2021/005527
§ 371 (c)(1),
(2) Date: Oct. 8, 2021

(87) PCT Pub. No.: WO2022/030730
PCT Pub. Date: Feb. 10, 2022

(65) Prior Publication Data
US 2023/0151082 A1    May 18, 2023

(30) Foreign Application Priority Data
Aug. 4, 2020    (KR) ........................ 10-2020-0097546

(51) Int. Cl.
| | |
|---|---|
| *C07K 16/18* | (2006.01) |
| *A61K 35/17* | (2015.01) |
| *A61P 35/00* | (2006.01) |
| *C07K 14/725* | (2006.01) |
| *C12N 5/0783* | (2010.01) |
| *C12N 15/86* | (2006.01) |

(52) U.S. Cl.
CPC .............. *C07K 16/18* (2013.01); *A61K 35/17* (2013.01); *A61P 35/00* (2018.01); *C07K 14/7051* (2013.01); *C12N 5/0636* (2013.01); *C12N 15/86* (2013.01); *C07K 2317/622* (2013.01); *C12N 2740/15043* (2013.01)

(58) Field of Classification Search
None
See application file for complete search history.

(56) References Cited

U.S. PATENT DOCUMENTS

| | | |
|---|---|---|
| 10,793,641 B2 | 10/2020 | Wang et al. |
| 10,851,175 B2 | 12/2020 | Kim et al. |

FOREIGN PATENT DOCUMENTS

| | | | |
|---|---|---|---|
| AU | 2018388079 A1 | 7/2020 | |
| KR | 1020170036503 A | 4/2017 | |
| KR | 1020180055824 A | 5/2018 | |
| KR | 1020200090598 A | 7/2020 | |
| WO | 2019124468 A1 | 6/2019 | |
| WO | 2020146182 A1 | 7/2020 | |
| WO | 2020153605 A1 | 7/2020 | |

OTHER PUBLICATIONS

Nichole Tucker (Mar. 17, 2022) "CAR T-Cell Therapy Shows 'Limited Success' in Solid Tumors, But 'Incremental Changes' Still Being Made", Targeted Oncology, from https://www.targetedonc.com/view/car-t-cell-therapy-shows-limited-success-in-solid-tumors-but-incremental-changes-still-being-made, 3 pages as printed.*
Yan, et al. (2023) "Current advances and challenges in CAR T-Cell therapy for solid tumors: tumor-associated antigens and the tumor microenvironment", Experimental Hematology & Oncology, 12:14, 18 pages.*
Aurore Morello et al., "Mesothelin-Targeted CARs: Driving T Cells to Solid Tumors," Cancer Discovery, Oct. 26, 2015, pp. OF1-OF15, DOI: 10.1158/2159-8290.CD-15-0583.
Daniel Steinbach et al., "Mesothelin, a possible target for immunotherapy, is expressed in primary AML cells," European Journal of Haematology, Jul. 2, 2007, vol. 79, pp. 281-286.
Eur J Cancer. Jan. 2008; 44(1): 46-53, Published online Oct. 22, 2007. doi: 10.1016/j.ejca.2007.08.028.
KR Decision to grant dated Sep. 27, 2021 of KR App. No. 10-2021-0056873.
Louis A. Dainty et al., "Overexpression of folate binding protein and mesothelin are associated with uterine serous carcinoma," Gynecologic Oncology, Apr. 2, 2007, vol. 105, pp. 563-570.
Raffit Hassan et al., "Mesothelin Immunotherapy for Cancer: Ready for Prime Time?," J. Clin. Oncol., Dec. 1, 2016, vol. 34, No. 34, pp. 4171-4179.
Raffit Hassan et al., "Mesothelin targeted cancer immunotherapy," Eur J Cancer, Oct. 22, 2007, vol. 44, pp. 46-53.
Yue Hea et al., "Killing cervical cancer cells by specific chimeric antigen receptor-modified T cells," Journal of Reproductive Immunology, 2020, vol. 139, No. 103115, pp. 1-9.
AU Search Report dated Dec. 6, 2021 for AU Patent Application No. 2021245153.
Hua Jiang et al., "Efficient growth suppression in pancreatic cancer PDX model by fully human anti-mesothelin CAR-T cells", Protein & Cell, 2017, vol. 8, No. 12, pp. 926-931, DOI:10.1007/s13238-017-0472-9.
Leila Jafarzadeh et al., "Construction and Functional Characterization of a Fully Human Anti-mesothelin Chimeric Antigen Receptor (CAR) Expressing T Cell," Iran J. Allergy Asthma Immunol., Jun. 2020, vol. 19, No. 3, pp. 264-275, DOI: 10.18502/ijaai.v19i3.3454.
Jiang LV et al., "Mesothelin is a target of chimeric antigen receptor T cells for treating gastric cancer," Journal of Hematology & Oncology, 2019, vol. 12, article 18, 14 pages, DOI:10.1186/s13045-019-0704-y.
Seiji Okada et al., "Application of Highly Immunocompromised Mice for the Establishment of Patient-Derived Xenograft (PDX) Models," Cells, Aug. 13, 2019, pp. 1-18, vol. 8, No. 889.

\* cited by examiner

*Primary Examiner* — Robert M Kelly
(74) *Attorney, Agent, or Firm* — CANTOR COLBURN LLP

(57) ABSTRACT

Provided is an anti-mesothelin chimeric antigen receptor specifically binding to mesothelin. The anti-mesothelin chimeric antigen receptor according to an aspect exhibits an ability to specifically bind to mesothelin, and thus may be usefully applied to preventing or treating mesothelin-overexpressing cancers.

19 Claims, 19 Drawing Sheets

Specification includes a Sequence Listing.

ANTI-MESOTHELIN CHIMERIC ANTIGEN RECEPTOR SPECIFICALLY BINDING TO MESOTHELIN

CROSS REFERENCE TO RELATED APPLICATIONS

This application is a National Stage application of PCT/KR2021/005527, filed on Apr. 30, 2021, which claims priority to and the benefit of KR 10-2020-0097546, filed on Aug. 4, 2020, the disclosures of which are incorporated by reference herein in their entirety.

INCORPORATION-BY-REFERENCE OF MATERIAL SUBMITTED ELECTRONICALLY

Incorporated by reference in its entirety herein is a computer-readable nucleotide/amino acid sequence listing submitted herewith and identified as follows: 22,647 bytes ASCII document, named YPL2781US_Sequence_List_ST25.TXT, prepared on Aug. 24, 2022.

TECHNICAL FIELD

The present disclosure relates to an anti-mesothelin chimeric antigen receptor specifically binding to mesothelin.

BACKGROUND ART

Although anticancer immuno-therapeutic agents such as immune checkpoint inhibitors and CAR-T cell therapies have been proven to be effective in various cancers, it is reported that solid cancers do not significantly respond to these new types of anticancer immuno-therapeutic agents. This is presumably because the fibrous tissue surrounding the tumor interferes with responses to the immunotherapy, and makes it difficult to deliver the drug. Therefore, as a specific and more effective CAR-T cancer treatment method, there is a need to develop an antibody targeting a protein specifically overexpressed on the surface of solid cancer cells as a cancer antigen, and there is a growing need for studies on a method capable of effectively treating solid cancers using the antibody.

On the other hand, mesothelin is a glycosylphosphatidylinositol (GPI) domain-anchored glycoprotein present on the cell surface. Mesothelin is normally expressed at low levels in the mesothelium surrounding the cavities and internal organs of the human body, but is also known to be abundantly expressed in cancers, such as pancreatic cancer, mesothelioma, ovarian cancer, non-small cell lung cancer, etc.

DESCRIPTION OF EMBODIMENTS

Technical Problem

An aspect provides an anti-mesothelin antibody or an antigen-binding fragment thereof.

Another aspect provides an isolated nucleic acid encoding the anti-mesothelin antibody or antigen-binding fragment thereof.

Still another aspect provides a vector including the isolated nucleic acid.

Still another aspect provides a host cell transformed with the vector.

Still another aspect provides a method of preparing the anti-mesothelin antibody, the method including expressing the antibody by culturing the host cell.

Still another aspect provides a chimeric antigen receptor including an antigen-binding domain, a hinge domain, a transmembrane domain, and an intracellular signaling domain.

Still another aspect provides a polynucleotide encoding the chimeric antigen receptor.

Still another aspect provides a vector including the polynucleotide.

Still another aspect provides a cell transformed with the vector.

Still another aspect provides a pharmaceutical composition including the cell; medicinal use of the cell; and a method of preventing or treating cancer, the method including administering a therapeutically effective amount of the cells to an individual.

Other objects and advantages of the present disclosure will become more apparent from the following detailed description when taken in conjunction with the accompanying claims and drawings. Since contents that are not described in the present specification may be sufficiently recognized and inferred by those skilled in the art or similar art, a description thereof will be omitted.

Solution to Problem

Each description and embodiment disclosed in this application may be applied to other descriptions and embodiments. That is, all combinations of various elements disclosed in this application fall within the scope of the present application. Further, the scope of the present application is not limited by the specific description described below.

An aspect provides an anti-mesothelin antibody or an antigen-binding fragment thereof.

The "mesothelin (MSLN)" is a cell surface glycoprotein having a total amino acid length of 630aa (NCBI Gene ID: 10232), and is selectively expressed in some cells, particularly, in specific tumor cells. An amino acid sequence of the mesothelin protein is shown below.

```
                                      (SEQ ID NO: 40)
MALPTARPLLGSCGTPALGSLLFLLFSLGWQPSRTL

AGETGQEAAPLDGVLANPPNISSLSPRQLLGFPCA

EVSGLSTERVRELAVALAQKNVKLSTEQLRCLAHR

LSEPPEDLDALPLDLLLFLNPDAFSGPQACTRFFS

RITKANVDLLPRGAPERQRLLPAALACWGVRGSLL

SEADVRALGGLACDLPGRFVAESAEVLLPRLVSCP

GPLDQDQQEAARAALQGGGPPYGPPSTWSVSTMDA

LRGLLPVLGQPIIRSIPQGIVAAWRQRSSRDPSWR

QPERTILRPRFRREVEKTACPSGKKAREIDESLIF

YKKWELEACVDAALLATQMDRVNAIPFTYEQLDVL

KHKLDELYPQGYPESVIQHLGYLFLKMSPEDIRKW

NVTSLETLKALLEVNKGHEMSPQAPRRPLPQVATL

IDRFVKGRGQLDKDTLDTLTAFYPGYLCSLSPEEL

SSVPPSSIWAVRPQDLDTCDPRQLDVLYPKARLAF
```

-continued

```
QNMNGSEYFVKIQSFLGGAPTEDLKALSQQNVSMD

LATFMKLRTDAVLPLTVAEVQKLLGPHVEGLKAEE

RHRPVRDWILRQRQDDLDTLGLGLQGGIPNGYLVL

DLSMQEALSGTPCLLGPGPVLTVLALLLASTLA
```

Mesothelin exhibits low expression in normal mesothelial cells, but its high expression is observed in solid cancers (solid tumors), and its overexpression is observed in esophageal cancer, breast cancer, triple-negative breast cancer (TNBC), gastric cancer, cholangiocarcinoma, pancreatic cancer, colon cancer, lung cancer, thymic carcinoma, mesothelioma, ovarian cancer, endometrial cancer, cervical cancer, uterin serous carcinoma (USC), acute myeloid leukemia (AML), etc. (Cancer Discov. 2016 February; 6(2):133-46.; J Reprod Immunol. 2020; 139:103115.; Gynecol Oncol. 2007; 105(3):563-570.; Eur J Haematol. 2007; 79(4):281-286.).

In one exemplary embodiment, MSLN34, MSLN37 and MSLN38, which are antibodies specifically binding to a target antigen mesothelin, were prepared through panning of phage display antibody libraries.

As used herein, the term "antibody" collectively refers to a protein involved in biological immunity by selectively acting on an antigen, and the type thereof is not particularly limited. Heavy and light chains of an antibody including variable regions have antigen-binding sites recognizing epitopes, and the antibody exhibits antigen specificity according to sequence variation in the variable region. The variable region of the antigen-binding site is divided into a framework region (FR) with low variability and a complementarity determining region (CDR) with high variability. Heavy and light chains, each has three CDR regions, divided into CDR1, CDR2, and CDR3, and four FR regions. The CDRs of each chain are generally referred to as CDR1, CDR2, and CDR3, numbered sequentially starting from the N-terminus, and are also identified by the chain in which the particular CDR is located.

As used herein, the term "complementarity determining region" refers to a region conferring antigen-binding specificity in the variable region of an antibody.

As used herein, the term "epitope" refers to a specific three-dimensional molecular structure in an antigen molecule, to which an antibody is able to specifically bind.

The antibody includes all of a monoclonal antibody, a multispecific antibody, a human antibody, a humanized antibody, and a chimeric antibody (e.g., a humanized murine antibody). The antibody may also include a diabody, a triabody, and a tetrabody.

In the present disclosure, the antibody includes an "antigen-binding fragment" of the antibody or an "antibody fragment", which possesses antigen-binding ability. The antigen-binding fragment may be an antibody fragment including one or more complementarity determining regions, for example, selected from the group consisting of scFv, (scFv)2, scFv-Fc, Fab, Fab' and F(ab')2. Among the antibody fragments, Fab has a structure consisting of variable regions of a light chain and a heavy chain, a constant region of the light chain, and a first constant region of the heavy chain (CH1), and the Fab has one antigen-binding site. Fab' differs from Fab in that it has a hinge region including one or more cysteine residues at the C-terminus of the heavy chain CH1 domain. F(ab')2 antibody is produced when the cysteine residue in the hinge region of the Fab' forms a disulfide bond. Fv refers to a minimal antibody fragment having only a heavy chain variable region and a light chain variable chain. In the double-chain Fv (two-chain Fv), the heavy chain variable region and the light chain variable region are linked by a non-covalent bond. In the single-chain Fv (scFv), the heavy chain variable region and the light chain variable region are generally linked by a covalent bond via a peptide linker, or directly linked at the C-terminus, and thus a dimer-like structure such as double-chain Fv may be made.

The anti-mesothelin antibody or antigen-binding fragment thereof of an aspect may include a heavy chain CDR1 including an amino acid sequence consisting of SEQ ID NO: 1, a heavy chain CDR2 including an amino acid sequence consisting of SEQ ID NO: 2, a heavy chain CDR3 including an amino acid sequence consisting of SEQ ID NO: 3, and a light chain CDR1 including an amino acid sequence consisting of SEQ ID NO: 4, a light chain CDR2 including an amino acid sequence consisting of SEQ ID NO: 5, and a light chain CDR3 including an amino acid sequence consisting of SEQ ID NO: 6; or a heavy chain CDR1 including an amino acid sequence consisting of SEQ ID NO: 13, a heavy chain CDR2 including an amino acid sequence consisting of SEQ ID NO: 14, a heavy chain CDR3 including an amino acid sequence consisting of SEQ ID NO: 15, and a light chain CDR1 including an amino acid sequence consisting of SEQ ID NO: 16, a light chain CDR2 including an amino acid sequence consisting of SEQ ID NO: 17, and a light chain CDR3 including an amino acid sequence consisting of SEQ ID NO: 18.

The anti-mesothelin antibody or the antigen-binding fragment thereof may include a heavy chain variable region including a sequence having 80% or more sequence homology, specifically, 90% or more sequence homology, more specifically, 95% or more sequence homology, and much more specifically, 100% sequence homology to an amino acid sequence consisting of SEQ ID NO: 19 or 23.

The anti-mesothelin antibody or the antigen-binding fragment thereof may include a light chain variable region including a sequence having 80% or more sequence homology, specifically, 90% or more sequence homology, more specifically, 95% or more sequence homology, and much more specifically, 100% sequence homology to an amino acid sequence consisting of SEQ ID NO: 20 or 24.

The anti-mesothelin antibody or the antigen-binding fragment thereof may include a heavy chain variable region including an amino acid sequence consisting of SEQ ID NO: 19 and a light chain variable region including an amino acid sequence consisting of SEQ ID NO: 20.

The anti-mesothelin antibody or the antigen-binding fragment thereof may include a heavy chain variable region including an amino acid sequence consisting of SEQ ID NO: 23 and a light chain variable region including an amino acid sequence consisting of SEQ ID NO: 24.

In one specific embodiment, the anti-mesothelin antibody or the antigen-binding fragment thereof may be an anti-mesothelin scFv (anti-MSLN34 scFv) including the heavy chain variable region including the amino acid sequence consisting of SEQ ID NO: 19 and the light chain variable region including the amino acid sequence consisting of SEQ ID NO: 20.

In another specific embodiment, the anti-mesothelin antibody or the antigen-binding fragment thereof may be an anti-mesothelin scFv (anti-MSLN38 scFv) including the heavy chain variable region including the amino acid sequence consisting of SEQ ID NO: 23 and the light chain variable region including the amino acid sequence consisting of SEQ ID NO: 24.

The antibody or antigen-binding fragment thereof according to an aspect may include a sequence of anti-mesothelin-specific binding antibody described herein as well as biological equivalents thereof within a range that it may specifically recognize mesothelin. For example, the amino acid sequence of the antibody may be further given a change, in order to more improve the binding affinity and/or other biological characteristics of the antibody.

For example, the antibody may have a substitution in its amino acid sequence through conservative substitution. As used herein, the "conservative substitution" refers to a modification of a polypeptide, including substitution of one or more amino acids with amino acids having similar biochemical properties that do not result in loss of biological or biochemical function of the corresponding polypeptide. "Conservative amino acid substitution" refers to substitution whereby an amino acid residue is replaced by an amino acid residue having a similar side chain. Families of amino acid residues having similar side chains have been defined in the art. These families include amino acids with basic side chains (e.g., lysine, arginine, histidine), amino acids with acidic side chains (e.g., aspartic acid, glutamic acid), amino acids with uncharged polar side chains (e.g., glycine, asparagine, glutamine, serine, threonine, tyrosine, cysteine), amino acids with nonpolar side chains (e.g., alanine, valine, leucine, isoleucine, proline, phenylalanine, methionine, tryptophan), amino acids with beta-branched side chains (e.g., threonine, valine, isoleucine), and amino acids with aromatic side chains (e.g., tyrosine, phenylalanine, tryptophan, histidine). It may be expected that the antibody according to an aspect may still retain its original activity even though some amino acid sequences of the antibody are substituted through conservative amino acid substitutions.

Considering the variation having the above-mentioned biological equivalent activity, the antibody of an aspect or the nucleic acid molecule encoding the antibody is also interpreted to include sequences showing substantial identity with the sequences listed in the sequence listing. The substantial identity means a sequence showing at least 61% homology, more specifically, 70% homology, much more specifically, 80% homology, even much more specifically, 90% homology, even much more specifically, 95% homology, and even much more specifically, 98% homology, when aligning the sequence with any other sequence to maximally correspond to each other, and analyzing the aligned sequence using algorithms commonly used in the art. Alignment methods for sequence comparison are well known in the art.

Another aspect provides an isolated nucleic acid encoding the antibody or antigen-binding fragment thereof.

As used herein, the term "nucleic acid" has a meaning that comprehensively includes DNA and RNA molecules, wherein a nucleotide, a basic constituent unit in the nucleic acid molecule, includes not only a natural nucleotide, but also an analogue, in which a sugar or base is modified. Sequences of nucleic acids encoding the heavy chain and light chain variable regions of an aspect may be modified. The modification includes addition, deletion, or non-conservative substitution or conservative substitution of nucleotides.

The nucleic acid is also interpreted to include a nucleotide sequence showing substantial identity with respect to the nucleotide sequence of the nucleic acid. The substantial identity means a nucleotide sequence showing at least 80% homology, more specifically, at least 90% homology, and the most specifically, at least 95% homology, when aligning the nucleotide sequence of an aspect with any other sequence to maximally correspond to each other, and analyzing the aligned sequence using algorithms commonly used in the art.

Still another aspect provides a vector including the isolated nucleic acid. To express the antibody or the antibody fragment thereof in appropriate host cells, DNAs encoding partial or full-length light and heavy chains may be obtained by standard molecular biology techniques (e.g., PCR amplification or cDNA cloning using a hybridoma expressing a target antibody), and the vector may include essential regulatory elements operably linked such that the DNA (gene) insert may be expressed. The "operably linked" refers to a functional linkage between a nucleic acid expression control sequence and a nucleic acid sequence encoding a target protein or RNA in such a manner as to allow general functions, and means a linkage whereby a gene is expressed by the expression control sequence. The "expression control sequence" refers to a DNA sequence that controls expression of a DNA sequence operably linked in a specific host cell. Such control sequences include promoters for performing transcription, any operator sequences for controlling transcription, sequences encoding suitable mRNA ribosomal binding sites, sequences controlling termination of transcription and translation, initiation codons, stop codons, polyadenylation signal, enhancer, etc. Those skilled in the art may recognize that design of the expression vector may vary by selecting the control sequence depending on factors such as selection of host cells to be transformed, and expression levels of proteins, etc.

The type of the vector is not particularly limited, as long as it is a vector commonly used in the fields of cloning and antibody preparation, and examples thereof include, but are not limited to, a plasmid vector, a cosmid vector, a bacteriophage vector, a viral vector, etc. The plasmids include *E. coli*-derived plasmids (pBR322, pBR325, pUC118, and pUC119, pET-21b(+)), *Bacillus subtilis*-derived plasmids (pUB110 and pTP5), yeast-derived plasmids (YEp13, YEp24, and YCp50), etc. In addition, as the virus, such as retroviruses, adenoviruses, or animal viruses such as vaccinia viruses, insect viruses such as baculoviruses, etc. may be used. pComb3-based vectors commonly used in phage display, etc. may be used. Vectors commonly used to express antibodies in mammalian cells or to express proteins in mammalian cells, for example, pcDNA or pVITRO, may be used.

Still another aspect provides a host cell transformed with the vector.

As used herein, the term "transformation" refers to a molecular biological technique that changes genetic traits of cells by penetrating, between cells, a DNA chain fragment or plasmid having a foreign gene different from that originally possessed by cells and combining the DNA chain fragment or plasmid with DNA originally existing in the cells. The vector may be transfected into host cells. For transfection, a variety of different techniques commonly used to introduce exogenous nucleic acids (DNA or RNA) into prokaryotic or eukaryotic host cells, e.g., electrophoresis, calcium phosphate precipitation, DEAE-dextran transfection or lipofection, etc., may be used. The antibody or antigen-binding fragment thereof according to an aspect may be expressed in eukaryotic cells, specifically, mammalian host cells, considering applicability to microorganisms such as bacteria (*E. coli*) or yeasts, etc., or mammalian cells. The mammalian host cells may be, for example, any one selected from the group consisting of Chinese Hamster Ovary (CHO) cells, NSO myeloma cells, COS cells, SP2 cells, F2N cells, HEK293 cells, and antibody-producing hybridoma cells, but are not limited thereto.

Still another aspect provides a method of preparing the anti-mesothelin antibody, the method including expressing the antibody by culturing the host cell.

The method may include transforming the host cell for producing the antibody or antigen-binding fragment thereof of an aspect with a vector to which DNA encoding the antibody or antigen-binding fragment thereof is operably linked. The types of the selected host cell and recombinant expression vector are the same as described above, and the transforming may be performed by selecting an appropriate transformation method. When the recombinant expression vector encoding the antibody gene is introduced into mammalian host cells, the antibody may be produced by culturing the host cells for a period sufficient to allow the antibody to be expressed in the host cells, or more specifically, for a period sufficient to allow the antibody to be secreted into a culture medium where the host cells are cultured.

In addition, the method may further include culturing the transformed host cells to produce a polypeptide of the antibody or antigen-binding fragment thereof according to an aspect from the recombinant expression vector introduced into the host cells. The medium composition, culture conditions, and culture time for culturing the selected host cells may be appropriately selected. Antibody molecules produced in the host cells may be accumulated in the cytoplasm of the cells, secreted outside the cells or into the culture medium by an appropriate signal sequence, or targeted to the periplasm, etc. In addition, the antibody according to an aspect may be refolded using a method known in the art and allowed to have a functional structure such that it maintains binding specificity to mesothelin. In addition, when an antibody in the form of IgG is produced, heavy and light chains are expressed in separate cells, and then the heavy and light chains are brought into contact with each other in a separate step to form a complete antibody, or heavy and light chains are expressed in the same cells to form a complete antibody inside the cells.

In addition, the method may further include collecting the antibody or antigen-binding fragment thereof produced in the host cells. A method of collecting the antibody or antigen-binding fragment thereof produced in the host cells may be appropriately selected and controlled by considering characteristics of the polypeptide of the antibody or antigen-binding fragment thereof, characteristics of the host cells, expression patterns, targeting of the polypeptide, etc. For example, the antibody or antigen-binding fragment thereof secreted into the culture medium may be collected by a method of obtaining the culture medium culturing the host cells, and removing impurities by centrifugation, etc. As needed, to collect the antibodies by releasing, outside the cells, the antibodies present in specific organelles inside the cells or in the cytoplasm, cells may be lysed in a range that does not affect the functional structure of the antibody or antigen-binding fragment thereof.

The collected antibodies may be additionally subjected to a process of further removing impurities through a method such as chromatography, filtration by a filter, or dialysis, etc., and concentrating the product. Separation or purification of the collected antibodies may be performed by a separation or purification method commonly used for proteins, for example, by chromatography. The chromatography may include, for example, affinity chromatography including a protein A column, a protein G column, or a protein L column, ion exchange chromatography, or hydrophobic chromatography. In addition to the above chromatography, the antibody may be isolated and purified by combining filtration, ultrafiltration, salting out, dialysis, etc.

Still another aspect provides a chimeric antigen receptor including an antigen-binding domain, a hinge domain, a transmembrane domain, and an intracellular signaling domain.

Since the chimeric antigen receptor specifically binds to mesothelin, it includes an antigen-binding domain specifically binding to mesothelin.

The antigen-binding domain may include a heavy chain CDR1 including an amino acid sequence consisting of SEQ ID NO: 1, a heavy chain CDR2 including an amino acid sequence consisting of SEQ ID NO: 2, a heavy chain CDR3 including an amino acid sequence consisting of SEQ ID NO: 3, and a light chain CDR1 including an amino acid sequence consisting of SEQ ID NO: 4, a light chain CDR2 including an amino acid sequence consisting of SEQ ID NO: 5, and a light chain CDR3 including an amino acid sequence consisting of SEQ ID NO: 6; or a heavy chain CDR1 including an amino acid sequence consisting of SEQ ID NO: 13, a heavy chain CDR2 including an amino acid sequence consisting of SEQ ID NO: 14, a heavy chain CDR3 including an amino acid sequence consisting of SEQ ID NO: 15, and a light chain CDR1 including an amino acid sequence consisting of SEQ ID NO: 16, a light chain CDR2 including an amino acid sequence consisting of SEQ ID NO: 17, and a light chain CDR3 including an amino acid sequence consisting of SEQ ID NO: 18, which are the same as in the anti-mesothelin antibody or antigen-binding fragment thereof according to an aspect, and thus the redundant contents will be omitted.

As used herein, the term "chimeric antigen receptor (CAR)" refers to a structure of a chimeric antigen receptor by including an antigen-binding (recognizing) domain, a transmembrane domain, and an intracellular signaling domain.

In one specific embodiment, the antigen-binding fragment may be a single chain variable fragment (scFv).

The hinge domain, transmembrane domain, and intracellular signaling domain included in the chimeric antigen receptor are well known in the art.

The hinge domain is a domain that links the anti-mesothelin antibody or antigen-binding fragment thereof with the transmembrane domain, also called a spacer, and has the purpose of extending the antigen-binding domain from the T cell membrane. The hinge domain may be a CD8 hinge domain, an IgG1 hinge domain, an Ig4 hinge domain, a CD28 extracellular domain, a killer immunoglobulin-like receptor (KIR) extracellular domain, or a combination thereof, but is not limited thereto. Hinge domains commonly used in the art may be used.

The transmembrane domain may serve as a support for the chimeric antigen receptor molecule, and at the same time, may connect the hinge domain with the intracellular signaling domain. The transmembrane domain may penetrate the cell membrane of cells so that the anti-mesothelin antibody or antigen-binding fragment thereof of the chimeric antigen receptor is located on the cell surface and the intracellular signaling domain is located inside the cells. The transmembrane domain may be a transmembrane domain of CD3 zeta (CD3z), CD4, CD8, CD28, or KIR protein. Specifically, the transmembrane domain of CD8 or CD28 may be used. However, any transmembrane domain commonly used in the preparation of chimeric antigen receptors may be used without limitation.

The intracellular signaling domain receives signals transmitted by the anti-mesothelin antibody or antigen-binding fragment thereof, and delivers the signals into the cells to which the chimeric antigen receptor is bound. The intracellular signaling domain is not particularly limited to the type thereof, as long as it is a domain that transmits a signal capable of inducing T cell activation when the antibody binds to an antigen-binding site existing outside the cells. Various types of intracellular signaling domains may be used. The intracellular signaling domain may be, for example, an immunoreceptor tyrosine-based activation motif or ITAM, wherein the ITAM includes those derived from CD3 zeta, FcR gamma, FcR beta, CD3 gamma, CD3 delta, CD3 epsilon, CDS, CD22, CD79a, CD79b, CD66d, or FcεRIγ, but is not limited thereto.

In addition, the chimeric antigen receptor according to an aspect may further include a costimulatory domain together with the intracellular signaling domain.

The costimulatory domain, which is a domain that serves to transmit signals to T cells, in addition to signals by the intracellular signaling domain, refers to an intracellular domain of the chimeric antigen receptor, including an intracellular domain of the costimulatory molecule.

The costimulatory molecule, which is a cell surface molecule, refers to a molecule necessary to bring a sufficient response of lymphocytes to an antigen, and it may be, for example, CD27, CD28, 4-1BB, OX40, CD30, CD40, PD-1, ICOS, lymphocyte function-associated antigen-1 (LFA-1), CD2, CD7, LIGHT, NKG2C, or B7-H3, but is not limited thereto. The costimulatory domain may be an intracellular domain of a molecule selected from the group consisting of such costimulatory molecules and combinations thereof.

Each domain of the chimeric antigen receptor including the transmembrane domain and the intracellular signaling domain may be selectively linked via a short oligopeptide or polypeptide linker. The linker is not particularly limited to its length, as long as it is able to induce T cell activation through the intracellular domain when an antigen binds to an antibody located outside the cells, and any linker known in the art may be used.

In addition, the chimeric antigen receptor may include modified forms of the antibody and domains as described above. In this regard, the modification may be performed by substituting, deleting, or adding one or more amino acids in amino acid sequences of the wild-type antibody and domains without altering the functions of the antibody and domains. Generally, the substitution may be performed by substitution of alanine or conservative amino acid substitution that does not affect the charge, polarity, or hydrophobicity of the whole protein.

Still another aspect provides a polynucleotide encoding the chimeric antigen receptor.

With regard to the polynucleotide, various alterations may be made in the coding region within a range that does not change the amino acid sequence of the antigen receptor expressed from the coding region, and various alterations or modifications may also be made in the region excluding the coding region, within a range that does not affect the gene expression, due to codon degeneracy or considering codons preferred by an organism in which the antigen receptor is intended to express. A person skilled in the art may understand that such a modified polynucleotide is also included in the scope of the present disclosure. In other words, the polynucleotide according to an aspect may be modified by substitution, deletion, or insertion of one or more nucleic acid bases, or a combination thereof, as long as it encodes a protein having equivalent activity thereto, and these are also included within the scope of the present disclosure.

Still another aspect provides a vector including the polynucleotide and a cell transformed with the vector.

As the vector, a variety of vectors known in the art may be used, and expression control sequences, such as promoters, terminators, enhancers, etc., a sequence for membrane targeting or secretion may be appropriately selected depending on the type of host cell to produce the antigen receptor, and variously combined according to the purpose. The vector of the present disclosure includes a plasmid vector, a cosmid vector, a bacteriophage vector, and a virus vector, but is not limited thereto. Appropriate vectors include a signal sequence or leader sequence for membrane targeting or secretion, in addition to expression control elements such as a promoter, an operator, an initiation codon, a stop codon, a polyadenylation signal, and an enhancer, and may be prepared in various ways depending on the purpose.

In addition, the vector may be introduced into cells to transform the cells, and the cells may be, but are not limited to, T cells, NK cells, NKT cells, or gamma delta T cells (γδ T cells). The cells may be obtained or prepared from bone marrow, peripheral blood, peripheral blood mononuclear cells, or umbilical cord blood.

Still another aspect provides a pharmaceutical composition including the cells; medicinal use of the cells; and a method of preventing or treating cancer, the method including administering a therapeutically effective amount of the cells to an individual.

Since the pharmaceutical composition uses the aforementioned cells, the descriptions of overlapping contents therebetween will be omitted to avoid excessive complexity of the present disclosure.

The pharmaceutical composition or the medicinal use may be for preventing or treating cancer.

As used herein, the term "preventing" means all of the actions by which occurrence of cancer (tumor) is restrained or retarded by administering the pharmaceutical composition according to the present disclosure.

As used herein, the term "treating" means all of the actions by which symptoms of cancer (tumor) have taken a turn for the better or been modified favorably by administering the pharmaceutical composition according to the present disclosure.

As used herein, the term "individual" refers to a subject in need of treatment of a disease, and more specifically, mammals such as humans or non-human primates, rodents (rats, mice, guinea pigs, etc.), mouse, dogs, cats, horses, cattle, sheep, pigs, goats, camels, antelopes, etc.

As used herein, the term "cancer" collectively refers to diseases caused by cells having aggressive characteristics in which the cells ignore normal growth limits to divide and grow, invasive characteristics to infiltrate surrounding tissues, and metastatic characteristics of spreading to other sites in the body. In the present disclosure, the cancer is used in the same sense as a malignant tumor, and may be a mesothelin-positive or mesothelin-overexpressing cancer.

The cancer may be specifically a solid cancer, for example, more specifically a mesothelin-positive or mesothelin-overexpressing solid cancer. For example, the solid cancer may be any one selected from the group consisting of esophageal cancer, breast cancer, triple-negative breast cancer (TNBC), gastric cancer, cholangiocarcinoma, pancreatic cancer, colon cancer, lung cancer, thymic carcinoma, mesothelioma, ovarian cancer, endometrial cancer, cervical cancer, uterin serous carcinoma (USC), and acute myeloid leukemia (AML), but is not limited thereto.

In one specific embodiment, with respect to mesothelin-overexpressing solid cancers, cell killing effects on ovarian cancer, mesothelioma, and pancreatic cancer by administration of anti-MSLN-CAR-T cells were confirmed.

The pharmaceutical composition may include 10% by weight to 95% by weight of the cells according to one aspect as an active ingredient, based on the total weight of the pharmaceutical composition. In addition, the pharmaceutical composition of the present disclosure may further include one or more active ingredients exhibiting the same or similar function, in addition to the above active ingredient.

An administration dose of the cells may be adjusted depending on various factors including the type of disease, severity of the disease, the type and content of active ingredients and other ingredients included in the pharmaceutical composition, the type of formulation, and a patient's age, weight, general health conditions, gender, and diet, administration time, administration route, treatment period, and drugs concurrently used. However, for a desirable effect, the effective amount of the cells included in the pharmaceutical composition according to the present disclosure may be $1\times10^5$ cells/kg to $1\times10^{11}$ cells/kg. In this regard, the administration may be performed once a day, or divided into several administrations. Effective amounts of the cells or the pharmaceutical composition presented herein may be empirically determined without undue experimentation.

The pharmaceutical composition may be a formulation having a dosage form suitable for the purpose, according to a common method in the pharmaceutical field. In addition, the composition may be administered by formulating it into a unit dosage form suitable for administration into a patient's body according to a common method in the pharmaceutical field. The pharmaceutical formulation may further include, in addition to the active ingredient, one or more pharmaceutically acceptable common inert carriers, for example, a preservative, an analgesic, a solubilizer, or a stabilizer, etc. in the case of injectable formulations, and a base, an excipient, a lubricant, a preservative, etc. in the case of formulations for topical administration.

Further, the cells or the pharmaceutical composition including the same may be administered to an individual according to various methods known in the art, for example, intraperitoneally, intravenously, intramuscularly, subcutaneously, intradermally, orally, topically, intranasally, intrapulmonary, rectally, etc., but is not limited thereto.

Advantageous Effects of Disclosure

An anti-mesothelin chimeric antigen receptor according to an aspect exhibits a specific binding affinity for mesothelin, and thus may be usefully applied to preventing or treating mesothelin-overexpressing cancers.

MODE OF DISCLOSURE

Hereinafter, an aspect will be described in more detail with reference to exemplary embodiments. However, these exemplary embodiments are only for illustrating an aspect, and the scope of an aspect is not limited to these exemplary embodiments, and exemplary embodiments of an aspect are provided to more completely explain an aspect to a person having ordinary knowledge in the art.

Example 1: Panning of Phage Display Antibody Libraries

Figure 1:
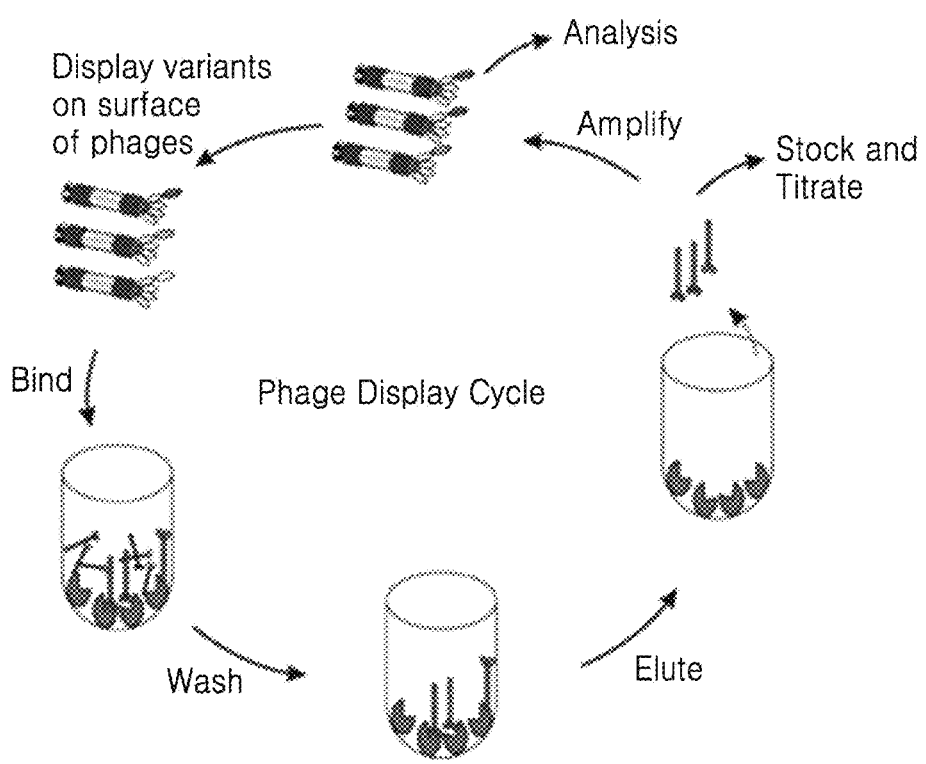
FIG. 1 shows an illustration showing a process of screening for antibodies through panning of phage display antibody libraries.

To select antibodies binding to mesothelin (MSLN) which is a target antigen, four rounds of phage panning for MSLN (Acro Biosystems) were performed using KBIO human synthetic scFv phage display library KscFv-I according to a phage panning protocol established by New Drug Development Support Center, Osong Advanced Medical Industry Promotion Foundation. A schematic illustration of the panning process of phage display antibody libraries is shown in FIG. 1.

Panning was performed by two methods (solid, bead) according to antigen immobilization. For solid phase panning, 1 mL of a human mesothelin protein (in PBS, $1^{st}$: 10 μg/mL, $2^{nd}$: 5 μg/mL, $3^{rd}$: 2.5 μg/mL, $4^{th}$: 1.25 μg/mL) was fixed in an immunotube, and mixed with $1.3 \times 10^{13}$ c.f.u. of phage library blocked with 5 mL of PBS (MPBS) containing 5% skim milk in the immunotube, and allowed to bind at 37° C. for 1.5 hours. Thereafter, the immunotube was washed with 5 mL of PBS-Tween20 (0.05%) (PBS-T) to remove unbound phages ($1^{st}$: washed three times, $2^{nd}$ to $4^{th}$: washed five times). 1 mL of 100 mM trimethylamine (TEA) was added to the tube, and allowed to react at room temperature for 10 minutes to elute bound phages, and the eluted phages were transferred to a 50 mL Falcon tube, and neutralized by mixing well with 0.5 mL of 1 M Tris-HCl (pH 7.4). The eluted phages were transfected to 8.5 mL of *E. coli* TG1 (OD600=0.5~0.8) at a mid-log phase. Plasmid DNA was extracted from a portion of the transfected *E. coli* TG1 for sequencing, and a portion thereof was subjected to antibody screening through phage ELISA. In the magnetic bead-mediated solution panning, the same protocol as in the solid phase panning was performed, except that magnetic beads, instead of the immunotube, were treated with the mesothelin, which was then fixed. In common, during panning, panning of a PBS control to which MSLN protein was not fixed was also performed, and its output titer was compared at every round of panning, and the degree of phage enrichment was monitored through an elution titer ratio (a value obtained by dividing the output titer by the output titer of the control group). The results are shown in FIGS. 2 and 3.

Figure 2A:
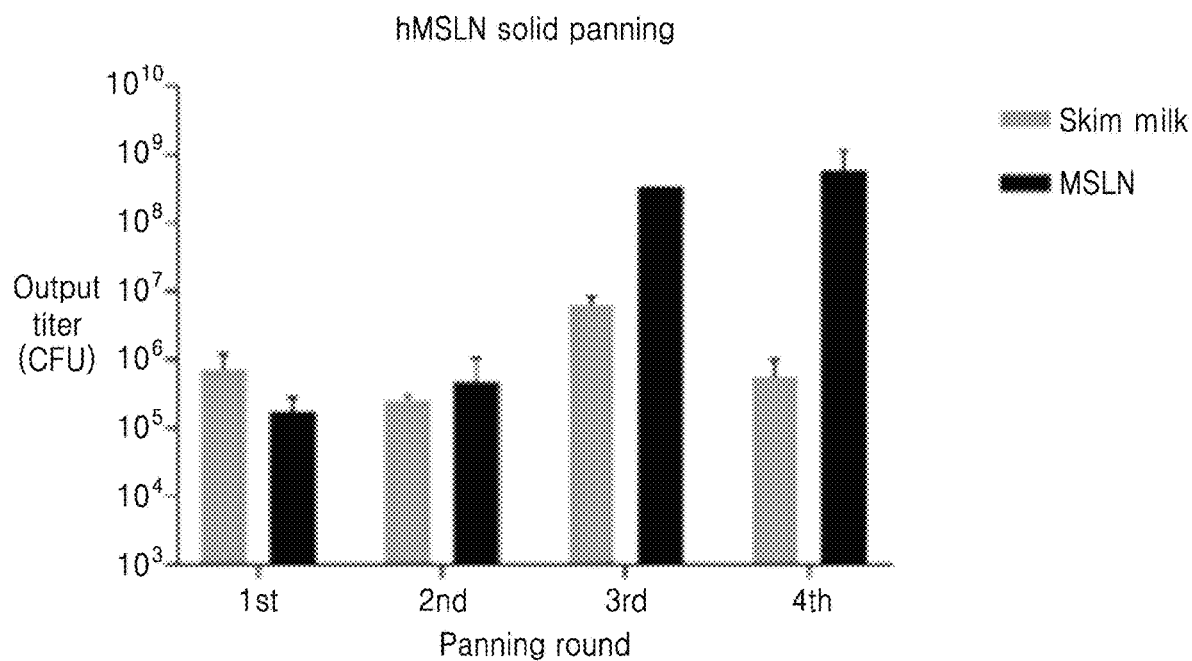
FIG. 2A shows a phage output titer and FIG. 2B shows an elution titer ratio, according to rounds of panning as a result of solid phase panning.
Figure 2B:
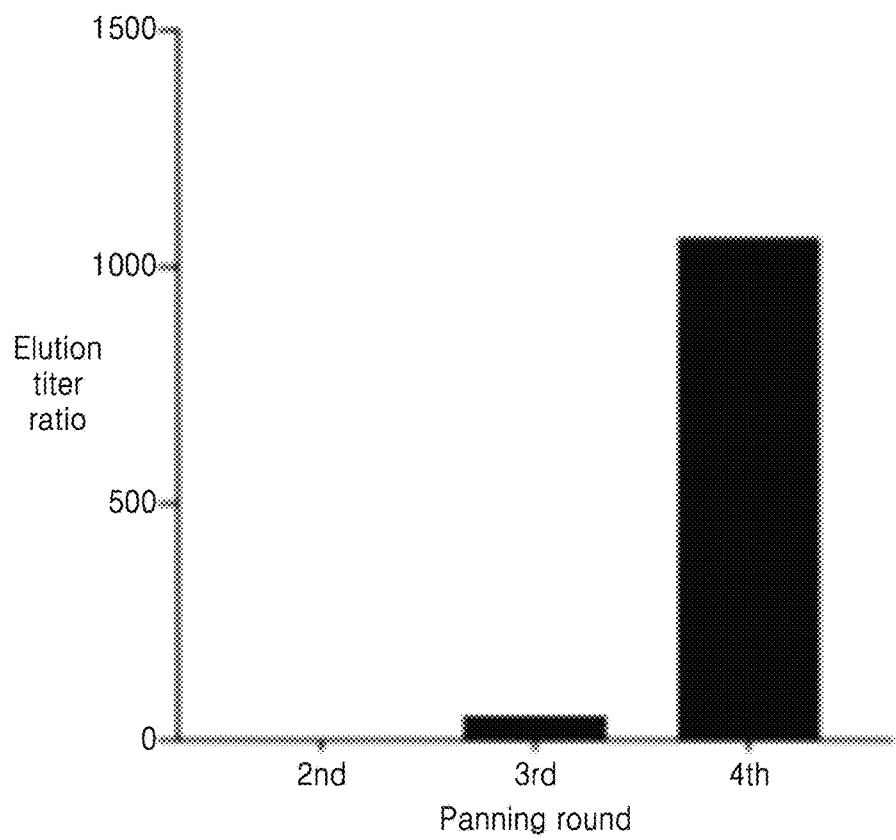
Figure 3A:
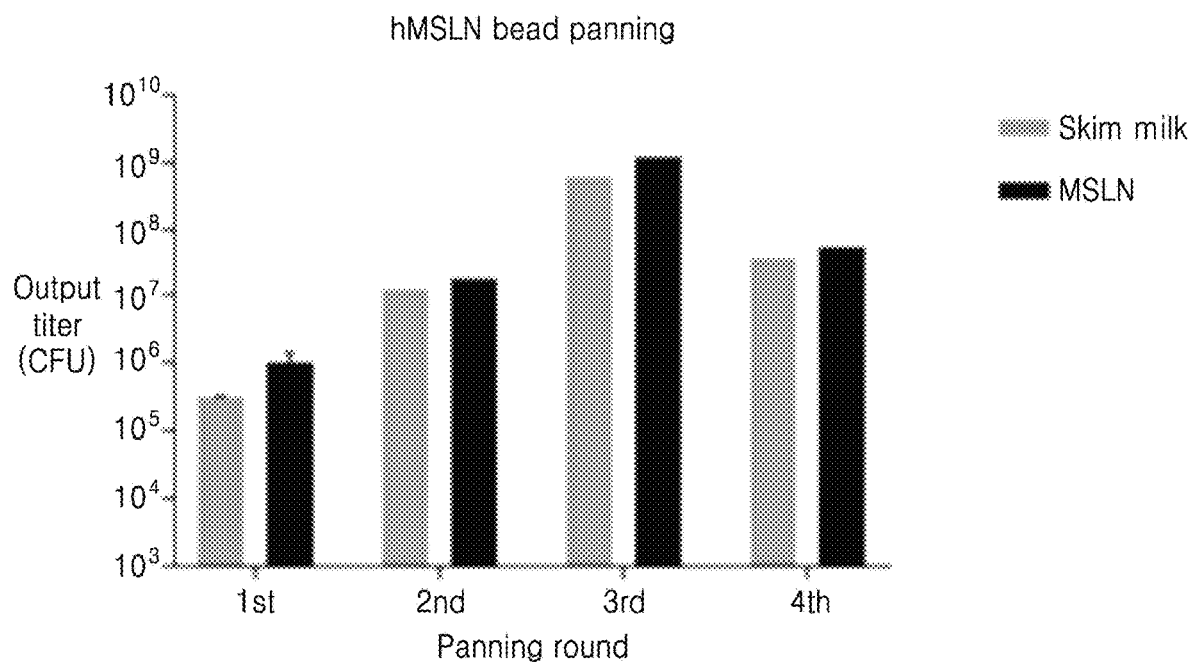
FIG. 3A shows a phage output titer and FIG. 3B shows an elution titer ratio, according to rounds of panning as a result of magnetic bead-mediated solution panning.
Figure 3B:
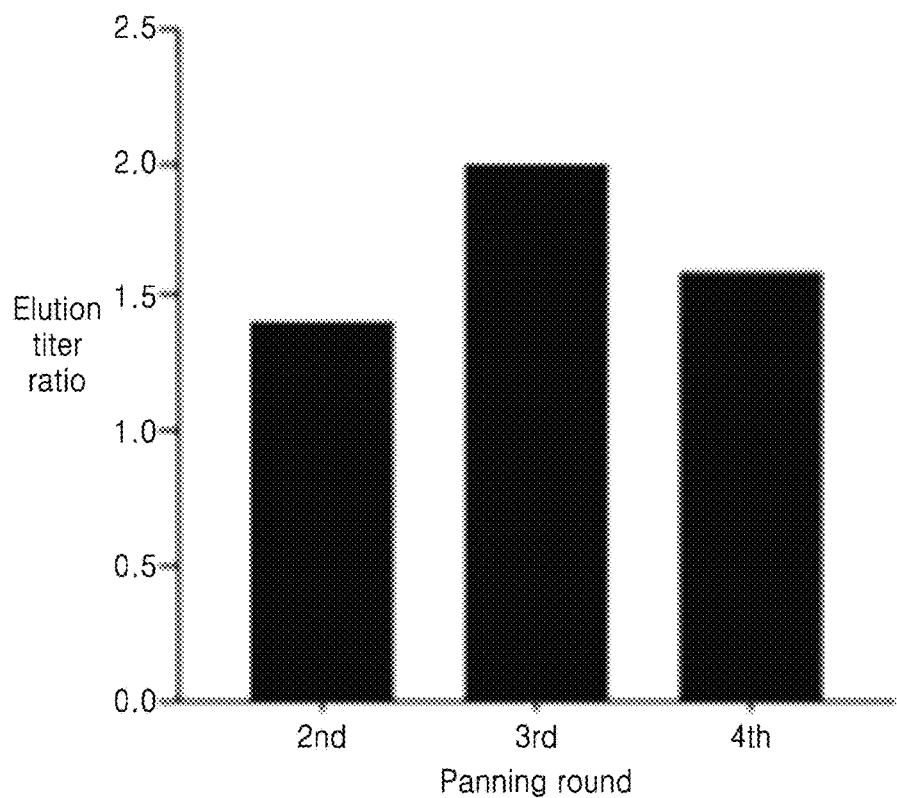

In the solid phase panning, the enrichment started from the $3^{rd}$ round, and the output titer for antigen MSLN showed a significant difference of about 53.4-fold ($3^{rd}$ round) and 1061.6-fold ($4^{th}$ round), as compared with the PBS control group (FIG. 2). In the panning using magnetic beads, the enrichment degrees of antigen MSLN at the $3^{rd}$ round and the $4^{th}$ round were about 2.0-fold ($3^{rd}$) and 1.6-fold ($4^{th}$), as compared with those of the PBS control group (FIG. 3), indicating no difference.

Example 2: Selection of Positive Clone by Phage-Specific ELISA

To select clones specifically binding to antigen MSLN from the phages obtained according to the phage panning of Example 1, 282 clones (94 colonies×3 plates) obtained from the $2^{nd}$ round of panning using the immunotube were subjected to single-clone phage ELISA. In detail, 30 μL of 1 μg/mL human MSLN protein (antigen) was added to each well of a 96-half-well ELISA plate, and coated by incubation at 4° C. overnight. As a negative control, 30 μL of PBS was added to each well of another plate, followed by incubation at 4° C. overnight. Next day, contents in the plate were removed, and the plate was blocked with 150 μL of 5% MPBS at room temperature for 1 hour. Then, contents in the plate were removed, and 30 μL of the phage (~$10^{11}$ c.f.u.) was added, followed by incubation at room temperature for 1.5 hours. As a negative control, 30 μL of PBS, instead of the phage, was added. The plate was washed with a PBS-T (PBS-0.05% Tween 20) solution four times, and anti-M13-HRP (diluted 1:5,000 in PBS) was added and incubated at 37° C. for 1 hour. The plate was washed with the PBS-T solution four times, and 30 μL of TMB substrate reagent was added to each well, and incubated at room temperature for 8 minutes to induce color development. After stopping the color development by adding 30 μL of 2N H2SO4 per well, absorbance (O.D.) at 450 nm was measured.

As a result, when the absorbance cut-off for antigen MSLN was set at 0.4 or higher and the selection was performed, respectively, a total of 56 positive clones were obtained in the $2^{nd}$ round. Additionally, the clones obtained in the $3^{rd}$ and $4^{th}$ rounds of panning using the immunotube were also subjected to single-clone phage ELISA in the same manner. 752 clones (94 colonies×8 plates) obtained in the $3^{rd}$ round of panning were subjected to phage ELISA, and the absorbance cut-off was set at 0.7 or 0.4 or higher, and selection was performed. As a result, a total of 173 positive clones were obtained. Further, 188 clones (94 colonies×2 plates) obtained in the $4^{th}$ round of panning were subjected to phage ELISA, and the absorbance cut-off was set at 0.4 or higher, and selection was performed. As a result, a total of 2 positive clones were obtained (Tables 1 to 4).

TABLE 1

| $2^{nd}$ round of panning (2 Round) | Absorbance (450 nm) | Number of positive clones | Number of unique clones |
|---|---|---|---|
| 2R-1 | >0.4 | 25 | 1 |
| 2R-2 | >0.4 | 14 | 1 |
| 2R-3 | >0.4 | 17 | 1 |
| Sum | | 56 | 3 |

TABLE 2

| $3^{rd}$ round of panning (3 Round) | Absorbance (450 nm) | Number of positive clones | Number of unique clones |
|---|---|---|---|
| 3R-6 | >0.7 | 6 | 0 |
| 3R-7 | >0.4 | 9 | 1 |
| 3R-8 | >0.4 | 40 | 1 |
| 3R-9 | >0.4 | 9 | 0 |
| 3R-10 | >0.4 | 31 | 3 |
| 3R-11 | >0.4 | 37 | 0 |
| 3R-12 | >0.4 | 23 | 1 |
| 3R-13 | >0.4 | 18 | 0 |
| Sum | | 173 | 6 |

TABLE 3

| $4^{th}$ round of panning (4 Round) | Absorbance (450 nm) | Number of positive clones | Number of unique clones |
|---|---|---|---|
| 4R-4 | >0.4 | 1 | 0 |
| 4R-5 | >0.4 | 1 | 0 |
| Sum | | 2 | 0 |

TABLE 4

| $2^{nd}$ + $3^{rd}$ + $4^{th}$ rounds of panning | Sum |
|---|---|
| Number of positive clones | 231 |
| Number of unique clones | 23 |
| Number of unique clones (excluding overlapping clones) | 9 |

Next, to further select clones specifically binding to antigen MSLN from the phages obtained according to the phage panning of Example 1, the clones obtained in the $3^{rd}$ and $4^{th}$ rounds of panning using the magnetic beads were also subjected to single-clone phage ELISA in the same manner. 188 clones (94 colonies×2 plates) obtained in the 3$^{rd}$ round of panning were subjected to phage ELISA, and the absorbance cut-off was set at 0.4 or higher, and selection was performed. As a result, a total of 4 positive clones were obtained. Further, 376 clones (94 colonies×4 plates) obtained in the 4$^{th}$ round of panning were subjected to phage ELISA, and the absorbance cut-off was set at 0.4 or higher, and selection was performed. As a result, a total of 7 positive clones were obtained (Tables 5 to 7).

TABLE 5

| 3$^{rd}$ round of panning (3 Round) | Absorbance (450 nm) | Number of positive clones | Number of unique clones |
|---|---|---|---|
| B-3R-1 | >0.4 | 4 | 2 |
| B-3R-2 | >0.4 | 0 | 0 |
| Sum | | 4 | 2 |

TABLE 6

| 4$^{th}$ round of panning (4 Round) | Absorbance (450 nm) | Number of positive clones | Number of unique clones |
|---|---|---|---|
| B-4R-1 | >0.4 | 0 | 0 |
| B-4R-2 | >0.4 | 2 | 2 |
| B-4R-3 | >0.4 | 5 | 3 |
| B-4R-4 | >0.4 | 0 | 0 |
| Sum | | 7 | 5 |

TABLE 7

| 3$^{rd}$ + 4$^{th}$ pounds of panning | Sum |
|---|---|
| Number of positive clones | 11 |
| Number of unique clones | 7 |
| Number of unique clones (excluding overlapping clones) | 7 |

Example 3: Sequencing and ELISA for Selecting Anti-MSLN Antibody Fragment Candidates Phages were recovered from a total of 415 positive clones selected in Example 2, and then DNA sequencing was performed, and the sequences were aligned and grouped according to the Kabat numbering system. As a result, 16 kinds of unique clones for the antigen MSLN, the clones having different CDR sequences, were selected. In order to examine the specific binding of 16 kinds of the clones to antigen MSLN, each phage was purified and the phage titer was equally adjusted (1.2E+11 pfu/well), and then compared through ELISA. As a negative control, TLR4 antigen conjugated to a histidine tag as in MSLN was used, and as a positive control, clone MSLN3, of which excellent binding ability to mesothelin was confirmed in a previous study, was used (see Table 8 below). The results are shown in FIG. 4.

TABLE 8

| Clone | Region | Amino acid sequence | SEQ ID NO: |
|---|---|---|---|
| MSLN3 | HCDR1 | DYAMS | 32 |
| | HCDR2 | AISSSGGTTYYADSVKG | 33 |
| | HCDR3 | EEEGEWREYFDV | 34 |
| | LCDR1 | RASQSISSYLN | 35 |
| | LCDR2 | ATSTLQS | 36 |
| | LCDR3 | QQSYTFPYT | 37 |
| | VH | EVQLVESGGGLVQPGGSL RLSCAASGFTFSDYAMSWVR QAPGKGLEWVSAISSSGGTT YYADSVKGRFTISRDNSKNT LYLQMNSLRAEDTAVYYCAK EEEGEWREYFDVWGQGTLVT VSS | 38 |
| | VL | DIQMTQSPSSLSASVGDR VTITCRASQSISSYLNWYQQ KPGKAPKLLIYATSTLQSGV PSRFSGSGSGTDFTLTISSL QPEDFATYYCQQSYTFPYTF GQGTKVEIK | 39 |

Figure 4:
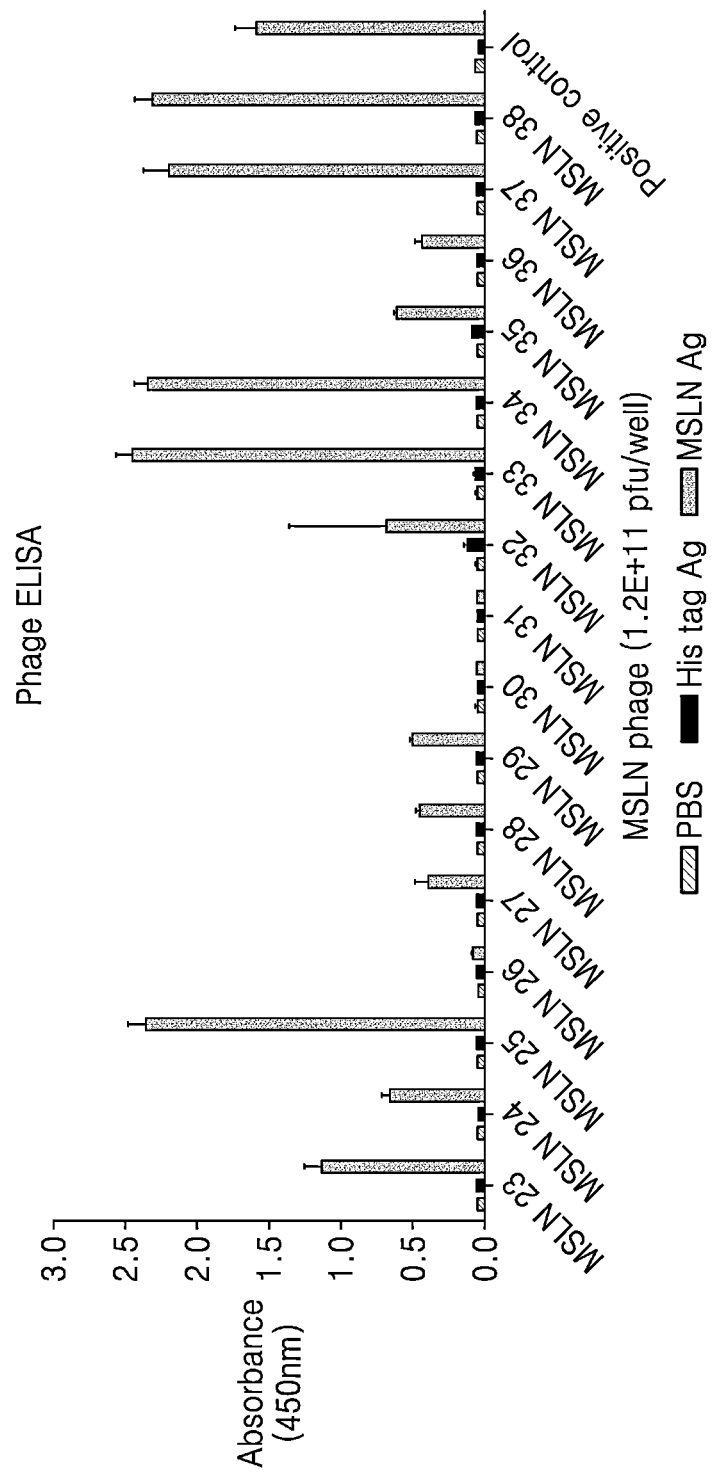
FIG. 4 shows results of comparative analysis of specific binding to antigen MSLN of clones obtained through phage ELISA.

As shown in FIG. 4, it was confirmed that among 16 kinds of clones, 13 clones, except for MSLN26, MSLN30, and MSLN31, specifically bind to the antigen MSLN.

Example 4: Examination of Binding Ability Using Mesothelin-Overexpressing Cell Line In order to determine whether 16 kinds of the phage clones selected in Example 3 actually bind to mesothelin present on the cell membrane, a pancreatic cancer cell line AsPC-1 which is a mesothelin-overexpressing cell line, and a human chronic myelogenous leukemia cell line K562 as a control were used to perform flow cytometry analysis.

In detail, K562 and AsPC-1 cells were prepared at a density of 10$^6$ cells/well, and washed with 300 μL of PBS. Cells were blocked with 300 μL of 4% MPBS at 4° C. for 30 min. At the same time, phage clones (10$^{12}$/well) were blocked at room temperature for 1 hour in the same manner, and then the phage were incubated together with the cells at 4° C. for 2 hours. The cells were washed with PBS, and then treated with 1 μg/mL of anti-M13-FITC, followed by incubation at 4° C. for 1 hour. The cells were washed with PBS, and then resuspended in PBS, and the results were analyzed using a flow cytometer (BD biosciences). The results are shown in FIGS. 5 and 6.

Figure 5:
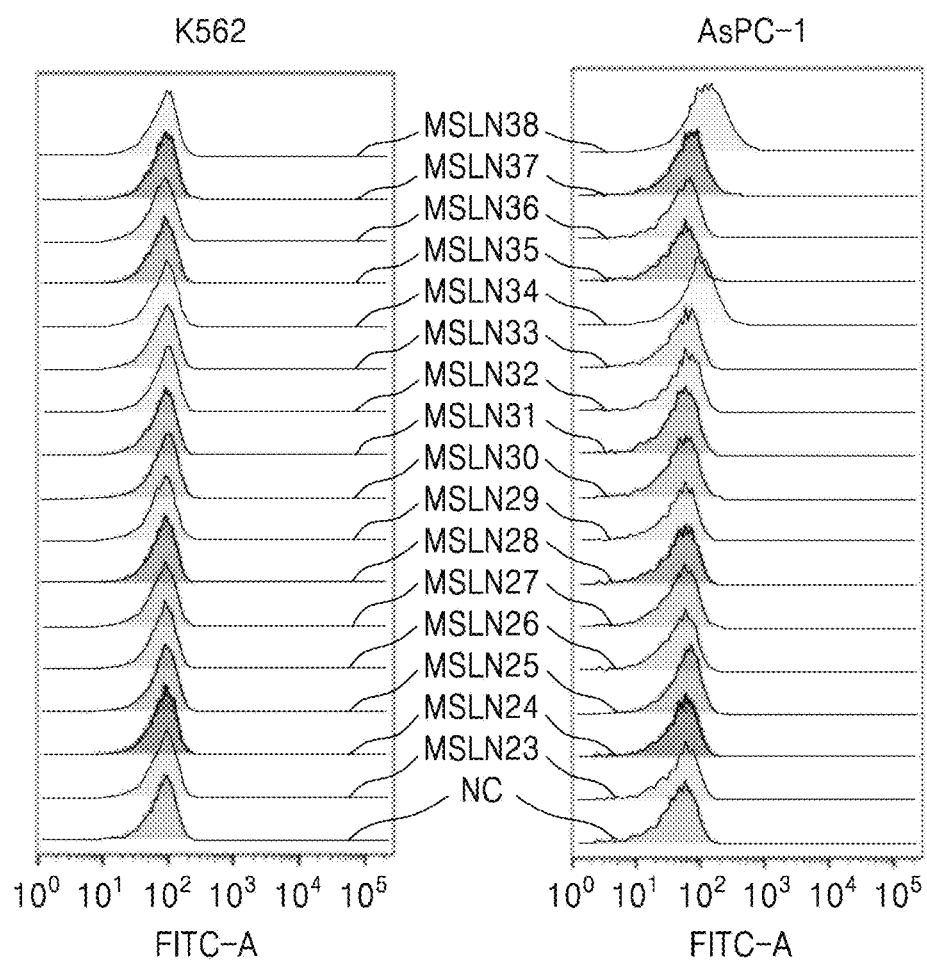
FIG. 5 shows flow cytometry results of examining whether clones selected using a mesothelin-overexpressing cell line actually bind to mesothelin present on the cell membrane.

As shown in FIG. 5, it was confirmed that MSLN34, MSLN37, and MSLN38 showed a relative peak shift value of 5.0% or more in the pancreatic cancer cell line AsPC-1. In the control K562 cell line, a significant level of peak shift was not observed. These results indicate that, among 16 kinds of clones, MSLN34, MSLN37, and MSLN38 actually exhibit high binding affinity for mesothelin present on the cell membrane.

Figure 6:
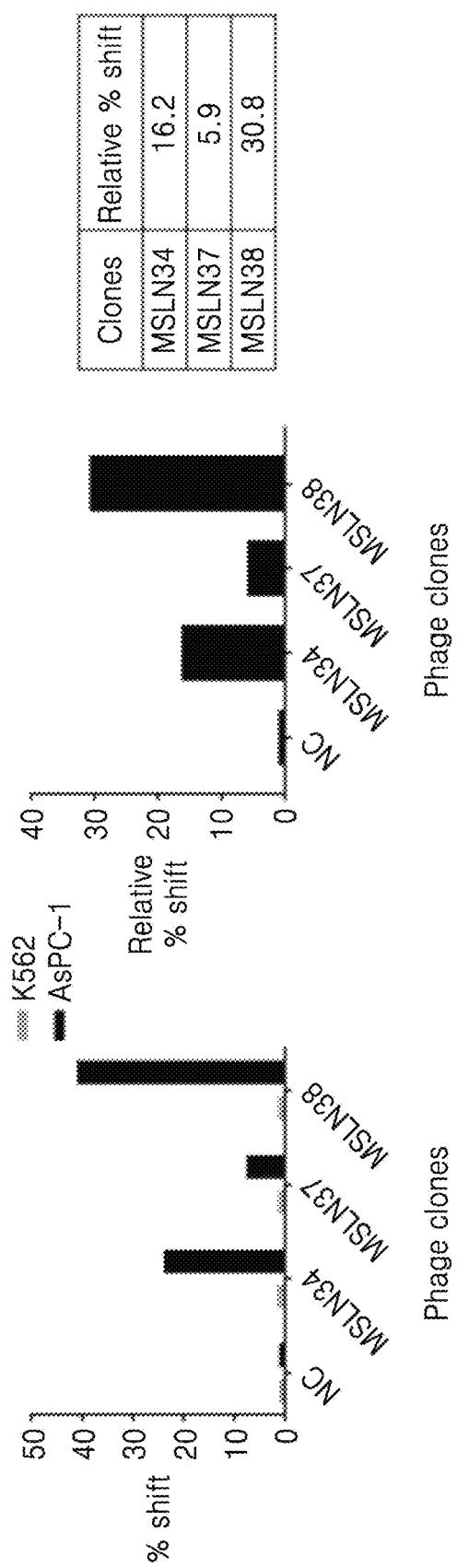
FIG. 6 shows relative peak shift values showing binding specificity to mesothelin of clones selected using a mesothelin-overexpressing cell line.

In addition, as shown in FIG. 6, when the results of flow cytometry were quantified, it was confirmed that MSLN34, MSLN37, and MSLN38 showed relative peak shift values of 16.2%, 5.9%, and 30.8%, respectively, as compared to the control K562 cells. These results confirmed that all three clones specifically bind to the mesothelin-overexpressing cell line, and finally, they were selected as clones for the production of anti-MSLN antibody fragments.

Example 5: Production and Purification of Anti-MSLN Antibody Fragment

Figure 7:
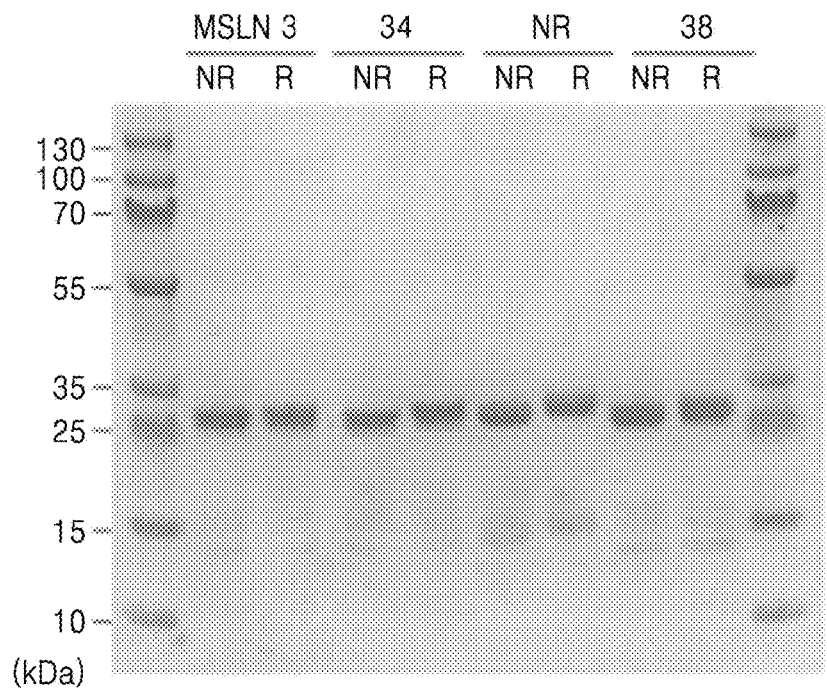
FIG. 7 shows SDS-PAGE results of analyzing purified anti-MSLN-scFv antibodies (2 µg of each protein loaded) (NR: Non-reducing condition, R: Reducing condition (100° C., 10 minutes))

The three kinds of clones selected in Example 4 were used to transform Top10F' competent *E. coli* which is an antibody fragment-expressing strain. Then, *E. coli* strains transformed with the three kinds of clones were cultured in 200 mL of TB medium, respectively, and protein expression was induced with IPTG (final concentration of 0.5 mM), followed by incubation at 30° C. overnight. Cells were obtained by centrifugation of the culture medium, and water-soluble proteins were obtained through periplasmic extraction, and then anti-MSLN-scFv antibody was purified through affinity chromatography using a protein L resin. The purified antibody protein was analyzed by SDS-PAGE, and the results are shown in FIG. 7.

Amino acid sequences of the three kinds of purified antibodies (MSLN34, MSLN37, and MSLN38) were examined and shown in Table 9, below. Specifically, heavy chain CDR1-3 amino acid sequences of MSLN34 are shown in SEQ ID NOS: 1 to 3, and light chain CDR1-3 amino acid sequences thereof are shown in SEQ ID NOS: 4 to 6, heavy chain CDR1-3 amino acid sequences of MSLN37 are shown in SEQ ID NOS: 7 to 9, and light chain CDR1-3 amino acid sequences thereof are shown in SEQ ID NOS: 10 to 12, and heavy chain CDR1-3 amino acid sequences of MSLN38 are shown in SEQ ID NOS: 13 to 15, and light chain CDR1-3 amino acid sequences thereof are shown in SEQ ID NOS: 16 to 18, respectively.

TABLE 9

| Clone | Region | Amino acid sequence | SEQ ID NO: |
|---|---|---|---|
| MSLN34 | HCDR1 | DYGMH | 1 |
| | HCDR2 | SIYGSGGHTGYADSVKG | 2 |
| | HCDR3 | QHAYRYSYAFDV | 3 |
| | LCDR1 | RASQSISNWLN | 4 |
| | LCDR2 | ATSSLQS | 5 |
| | LCDR3 | QQSYSFPFT | 6 |
| MSLN37 | HCDR1 | SYAMH | 7 |
| | HCDR2 | GISGSGGTTYYADSVKG | 8 |
| | HCDR3 | EVEGQSQEYFDI | 9 |
| | LCDR1 | RASQSIANYLN | 10 |
| | LCDR2 | AASNLQS | 11 |
| | LCDR3 | QQSYSFPYT | 12 |
| MSLN38 | HCDR1 | SYAMS | 13 |
| | HCDR2 | GISGSGGSTGYADSVKG | 14 |
| | HCDR3 | HGQVGGISVFDI | 15 |
| | LCDR1 | RASQSISNWLN | 16 |
| | LCDR2 | ATSRLQS | 17 |
| | LCDR3 | QQSYSFPWT | 18 |

TABLE 9-continued

| Clone | Region | Amino acid sequence | SEQ ID NO: |
|---|---|---|---|
| MSLN3 4 | VH | EVQLVESGGGLVQPGGSLRLSCAASGFTFSDYGMHW VRQAPGKGLEWVSSIYGSGGHTGYADSVKGRFTISRD NSKNTLYLQMNSLRAEDTAVYYCAKQHAYRYSYAFDV WGQGTLVTVSS | 19 |
|  | VL | DIQMTQSPSSLSASVGDRVTITCRASQSISNWLNWYQQ KPGKAPKLLIYATSSLQSGVPSRFSGSGSGTDFTLTISS LQPEDFATYYCQQSYSFPFTFGQGTKVEIK | 20 |
| MSLN3 7 | VH | EVQLVESGGGLVQPGGSLRLSCAASGFTFSSYAMHWV RQAPGKGLEWVSGISGSGGTTYYADSVKGRFTISRDN SKNTLYLQMNSLRAEDTAVYYCAKEVEGQSQEYFDIW GQGTLVTVSS | 21 |
|  | VL | DIQMTQSPSSLSASVGDRVTITCRASQSIANYLNWYQQ KPGKAPKLLIYAASNLQSGVPSRFSGSGSGTDFTLTISS LQPEDFATYYCQQSYSFPYTFGQGTKVEIK | 22 |
| MSLN3 8 | VH | EVQLVESGGGLVQPGGSLRLSCAASGFTFSSYAMSWV RQAPGKGLEWVSGISGSGGSTGYADSVKGRFTISRDN SKNTLYLQMNSLRAEDTAVYYCAKHGQVGGISVFDIWG QGTLVTVSS | 23 |
|  | VL | DIQMTQSPSSLSASVGDRVTITCRASQSISNWLNWYQQ KPGKAPKLLIYATSRLQSGVPSRFSGSGSGTDFTLTISS LQPEDFATYYCQQSYSFPWTFGQGTKVEIK | 24 |

Example 6: Analysis of Affinity of Anti-MSLN Antibody for Antigen

The three kinds of anti-MSLN antibody proteins prepared in Example 5 were used to compare and analyze affinity thereof for antigen MSLN through ELISA. In detail, a MaxiSorb ELISA plate (Nunc) was coated with 30 μL of human mesothelin protein at a concentration of 1 μg/mL per well, and incubated at 4° C. overnight. The contents in the plate were removed, and the plate was blocked with 300 μL of 5% MPBS at room temperature for 1 hour. The purified antibody was serially diluted with PBS, 30 μL thereof was added to each well, and incubated at room temperature for 2 hours. As a negative control, 60 μL of PBS, instead of the purified antibody, was added and incubated at 37° C. for 2 hours.

The plate was washed with a PBS-T (PBS-0.05% Tween 20) solution four times, and 30 μL of anti-StrepMAB HRP (diluted 1:5,000 in PBS) was added and incubated at room temperature for 1 hour. The plate was washed with the PBS-T solution four times, and 30 μL of TMB substrate reagent was added to each well, and incubated at room temperature for 8 minutes to induce color development. After stopping the color development by adding 30 μL of 2N H2SO4 per well, absorbance (O.D.) at 450 nm was measured. The results are shown in FIG. 8.

Figure 8A:
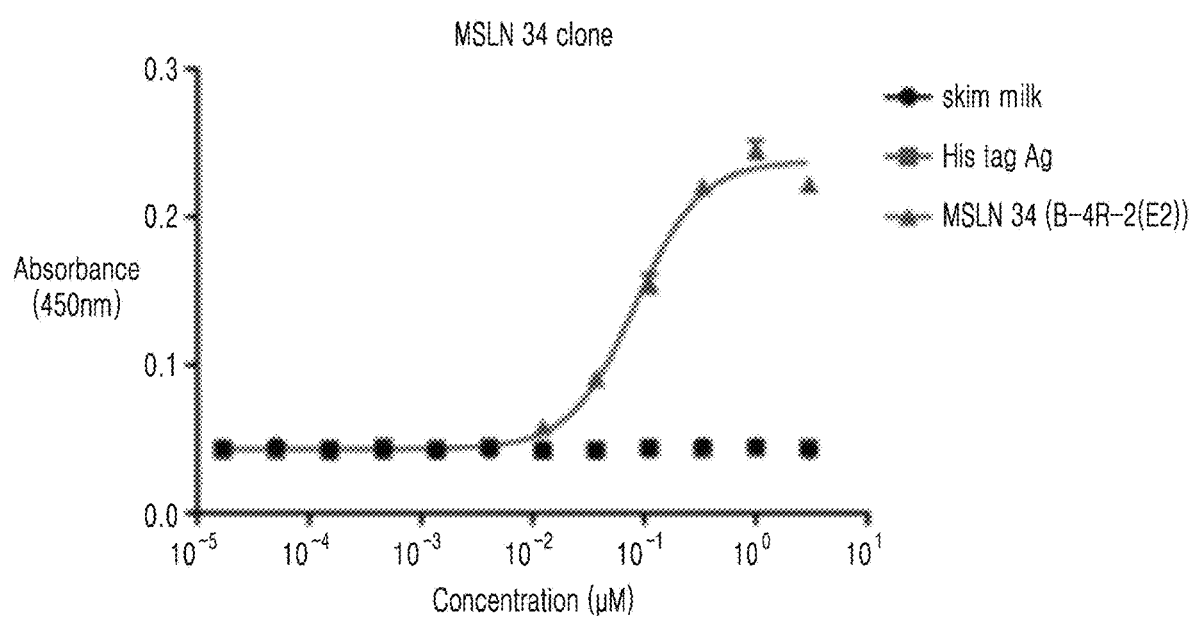
FIG. 8 shows ELISA results of analyzing affinity of anti-MSLN-scFv antibody for antigen MSLNs (A: MSLN 34 clone, B: MSLN 37 Clone, C: MSLN 38 Clone)
Figure 8B:
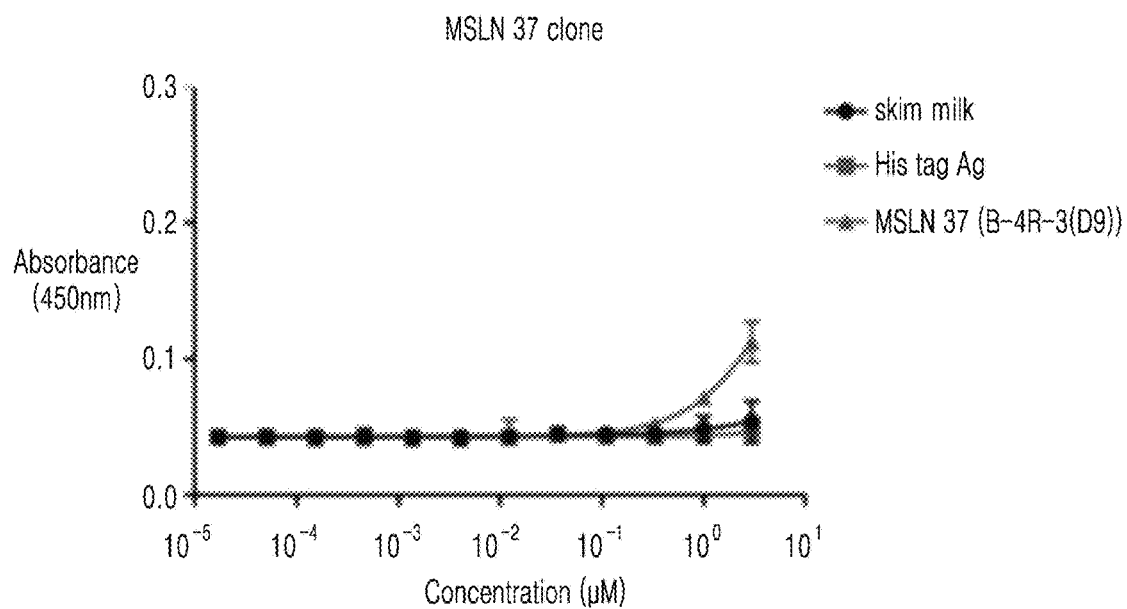
Figure 8C:
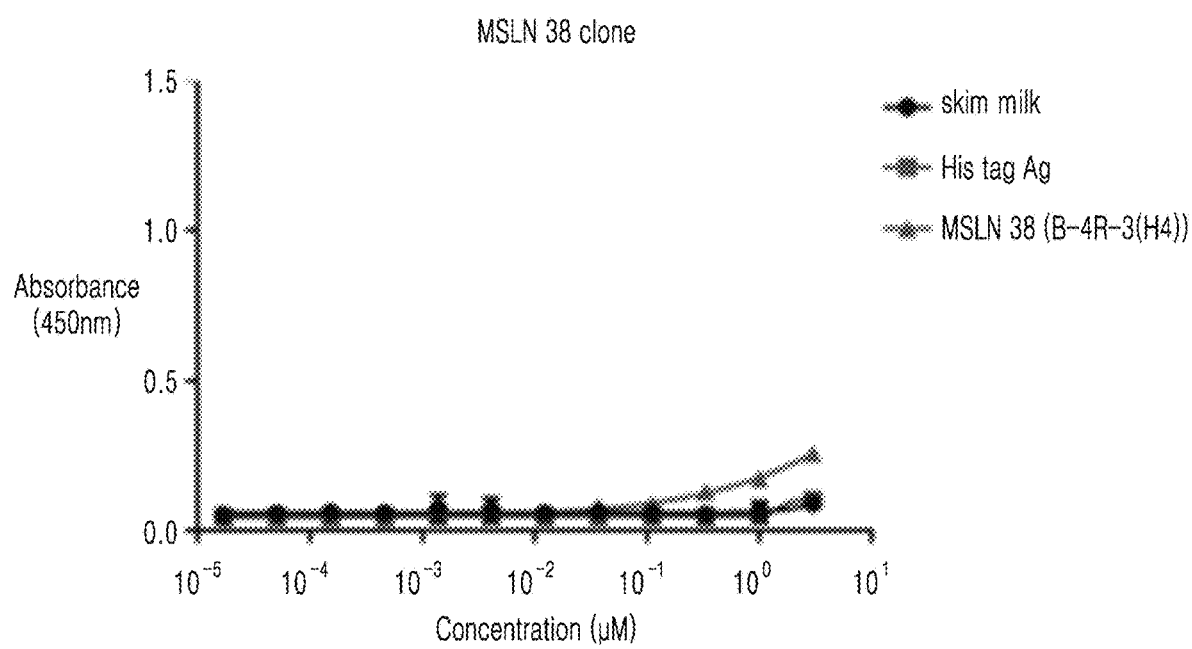

As shown in FIG. 8, it was confirmed that MSLN34 showed an $EC_{50}$ value of 83 nM, indicating the highest binding affinity among the three kinds of antibodies.

Example 7: Construction of Anti-MSLN Chimeric Antigen Receptor

Based on MSLN34 and MSLN38 showing high binding specificity to the mesothelin-overexpressing cell line, among the anti-MSLN antibody proteins prepared in Example 5, an anti-MSLN chimeric antigen receptor (anti-MSLN-CAR) was constructed.

7-1: Anti-MSLN-CAR Lentiviral Vector Cloning

The Vector Belongs to the Second-Generation CAR Lentiviral Vector (pLV Lentiviral vector) system owned by the New Drug Development Support Center, in which the system includes pMDLg/pRRE (addgene) encoding gag/pol, and an envelope plasmid pRSV-Rev (addgene) encoding Rev protein, and an envelope plasmid pMD2.G (addgene) encoding VSV-G protein.

First, gene cloning was performed for the anti-MSLN scFv (antigen-binding domain) prepared in Example 5. Each anti-MSLN scFv of MSLN34 and MSLN38 and lentiviral vector were digested with XhoI (R0146S, NEB) and EcoRI (R0101, NEB) at 37° C. for 2 hours, followed by agarose gel electrophoresis. The identified products were purified using a FavorPrep Gel/PCR purification Mini kit (Favorgen). Each purified anti-MSLN scFv (100 ng) and vector (50 ng) were ligated by reacting at a ratio of 2:1 at 16° C. for 16 hours, and then transformed into Stbl3 competent cells to obtain colonies. The colonies were taken and grown in 5 mL of LB medium (ampicillin) to obtain plasmid DNA using a DNA plasmid mini-prep method. The plasmid DNA was digested with XhoI and EcoRI to confirm whether each inserted anti-MSLN scFv was well cloned into the vector. After sequencing, the DNA sequence was finally identified.

To the anti-MSLN scFv, CD8 hinge and CD8 TM (transmembrane) as a transmembrane domain, a cytoplasmic region of 4-1BB as a signaling domain, and an intracellular domain of CD3 zeta (CD3z) as a T cell activation domain were sequentially linked to construct anti-MSLN-CAR. Specifically, anti-MSLN-CAR consists of a CD8 signal sequence (Signal peptide, SP) (SEQ ID NO: 25), an anti-MSLN34 scFv (SEQ ID NO: 26) or an anti-MSLN38 scFv (SEQ ID NO: 27), a CD8 hinge domain (SEQ ID NO: 28), a CD8 transmembrane domain (SEQ ID NO: 29), a 4-1BB signaling domain (SEQ ID NO: 30), and a CD3 zeta signaling domain (SEQ ID NO: 31). Each domain was sequentially linked using each restriction enzyme, and specific nucleotide sequence information corresponding to each domain is summarized in Table 10 below.

TABLE 10

| Name | Nucleotide sequence (5'-3') | SEQ ID NO: |
|------|------------------------------|------------|
| CD8 | ATGGCCTTACCAGTGACCGCCTTGCTCCTGCCGCTGGCCTT GCTGCTCCACGCCGCCAGGCCG | 25 |
| MSLN 34 scFv | GAAGTACAGTTGGTCGAAAGTGGCGGTGGCCTCGTGCAACC GGGTGGTTCACTGCGTCTGAGCTGCGCCGCCTCGGGTTTTA CTTTCTCTGATTATGGTATGCACTGGGTTCGTCAGGCGCCGG GCAAGGGTCTCGAATGGGTTTCATCTATCTACGGTTCTGGTG GTCACACTGGTTATGCCGATTCAGTGAAGGGTCGCTTTACCA TTTCCCGTGACAACTCTAAGAATACTCTGTATCTGCAGATGAA CTCGCTGCGTGCCGAAGACACGGCCGTCTATTATTGCGCCA AACAGCATGCATACCGTTACTCTTACGCATTCGATGTTTGGG GTCAGGGCACTTTAGTGACCGTCTCATCGGGTGGAGGCGGT TCAGGCGGAGGTGGATCCGGCGGTGGCGGATCGGACATTCA AATGACGCAGAGTCCCTCCTCACTGAGTGCTAGCGTGGGCG ATCGTGTGACAATTACTTGTCGCGCTAGCCAGTCTATCTCTAA TTGGCTGAACTGGTATCAGCAGAAACCGGGCAAGGCGCCAA AATTGCTGATTTACGCAACTTCCTCTCTGCAGTCTGGTGTACC GTCCCGTTTCTCTGGCAGCGGTTCTGGTACGGATTTTACCCT GACCATCTCAAGCCTCCAGCCTGAAGATTTTGCCACCTATTAT TGTCAGCAATCTTACTCTTTTCCGTTTACGTTCGGGCAGGGA ACTAAAGTGGAAATTAAAGCCAGCACC | 26 |
| MSLN 38 scFv | GAAGTACAGTTGGTCGAAAGTGGCGGTGGCCTCGTGCAACC GGGTGGTTCACTGCGTCTGAGCTGCGCCGCCTCGGGTTT1TA CTTTCTCTTCTTATGCAATGTCTTGGGTTCGTCAGGCGCCGG GCAAGGGTCTCGAATGGGTTTCAGGTATCTCTGGTTCTGGTG GTTCTACTGGTTATGCCGATTCAGTGAAGGGTCGCTTTACCA TTTCCCGTGACAACTCTAAGAATACTCTGTATCTGCAGATGAA CTCGCTGCGTGCCGAAGACACGGCCGTCTATTATTGCGCCA AACATGGTCAGGTTGGTGGTATCTCTGTTTTCGATATCTGGG GTCAGGGCACTTTAGTGACCGTCTCATCGGGTGGAGGCGGT TCAGGCGGAGGTGGATCCGGCGGTGGCGGATCGGACATTCA AATGACGCAGAGTCCCTCCTCACTGAGTGCTAGCGTGGGCG ATCGTGTGACAATTACTTGTCGCGCTAGCCAGTCTATCTCTAA TTGGCTGAACTGGTATCAGCAGAAACCGGGCAAGGCGCCAA AATTGCTGATTTACGCAACTTCCCGTCTGCAGTCTGGTGTAC CGTCCCGTTTCTCTGGCAGCGGTTCTGGTACGGATTTTACCC TGACCATCTCAAGCCTCCAGCCTGAAGATTTTGCCACCTATTA TTGTCAGCAATCTTACTCT11TCCGTGGACGTTCGGGCAGGG AACTAAAGTGGAAATTAAAGCCAGCACC | 27 |
| CD8 hinge | ACCACGACGCCAGCGCCGCGACCACCAACACCGGCGCCCA CCATCGCGTCGCAGCCCCTGTCCCTGCGCCCAGAGGCGTGC CGGCCAGCGGCGGGGGCGCAGTGCACACGAGGGGGCTG GACTTCGCCTGTGAT | 28 |
| CD8 TM | ATCTACATCTGGGCGCCCTTGGCCGGGACTTGTGGGGTCCT TCTCCTGTCACTGGTTATCACCCTTTACTGC | 29 |
| 4-1BB | AAACGGGGCAGAAGAAACTCCTGTATATATTCAAACAACCA TTTATGAGACCAGTACAAACTACTCAAGAGGAAGATGGCTGT AGCTGCCGATTTCCAGAAGAAGAAGAAGGAGGATGTGAACT G | 30 |
| CD3z | AGAGTGAAGTTCAGCAGGAGCGCAGACGCCCCGCGTACAC AGCAGGGCCAGAACCAGCTCTATAACGAGCTCAATCTAGGAC GAAGAGAGGAGTACGATGTTTTGGACAAGAGACGTGGCCGG GACCCTGAGATGGGGGGAAAGCCGAGAAGGAAGAACCCTCA GGAAGGCCTGTACAATGAACTGCAGAAAGATAAGATGGCGG AGGCCTACAGTGAGATTGGGATGAAAGGCGAGCGCCGGAGG GGCAAGGGGCACGATGCCTTTACCAGGGTCTCAGTACAGC CACCAAGGACACCTACGACGCCCTTCACATGCAGGCCCTGC CCCCTCGC | 31 |

7-2: Production of Anti-MSLN-CAR-Loaded Lentivirus

Figure 9:
FIG. 9 shows an illustration of an anti-MSLN-CAR expression system including an MSLN-specific antigen-binding domain according to an aspect.

Anti-MSLN-CAR lentivirus was produced by introducing the recombinant vector prepared in Example 7-1 into HEK293T cells. A schematic illustration of the anti-MSLN-CAR expression system according to an aspect, the system including the MSLN-specific antigen-binding domain, is shown in FIG. 9. First, the day before DNA transduction, HEK293T cells were seeded in a 100 mm tissue culture dish at a density of 6×10⁶ cells/dish. Next day, when the cell density reached 70% to 80%, transduction of MSLN-CAR-pLV, pMDLg/pRRE (addgene), pRSV-Rev (addgene), and pMD2.G (addgene) (5.5 μg: 3.5 μg:1.5 μg:2 μg) was performed using Lipofectamine 3000 (Thermofisher) according to the package insert. As a control, CD19 (FMC63) was used. 4 hours after transduction, DMEM medium containing 3% FBS (Gibco) was replaced, and after 48 hours, a virus culture medium was harvested. 10 mL of 20% sucrose solution was put in a centrifugation tube, 20 mL of the harvested virus culture medium was carefully placed thereon, and then mounted on a SW32T rotor, followed by ultra-high speed centrifugation at 25,000 rpm at 4° C. for 90 minutes. After centrifugation, the supernatant was discarded while being careful not to disturb the virus pellet at the bottom of the tube, and 400 μL of RPMI1640 medium (Gibco) was added and incubated in a refrigerator for 16 hours. Then, the pellet was resuspended and divided into 100 μL aliquots, which were then stored at −80° C.

7-3: Lentivirus Titration

One day before lentivirus infection, HeLa cells were seeded in a 6-well plate at a density of 1.5×10⁵ cells/well. Next day, virus was diluted 1/100 and 1/1,000 with 500 μL of a virus infection medium, and added together with 8 μg/mL of polybrene to infect the cells. In one well, cells were treated with Trypsin-EDTA (0.05%) and harvested, followed by cell counting. After 4 hours, 1 mL of the cell culture medium was added, and after 48 hours, the virus titer was determined by FACS analysis. The virus titer was calculated by the following equation.

$$\text{Virus titer (TU/mL)} = \text{Number of cells} \times \text{Percentage (\%) of FACS positive cells} \times \text{Dilution factor} \times 2 \quad \text{[Equation 1]}$$

As a result, it was confirmed that the virus titer of MSLN34-CAR scFv was $9.6 \times 10^7$ TU/mL, and the virus titer of MSLN38-CAR scFv was $1.6 \times 10^8$ TU/mL.

Example 8: Preparation of Anti-MSLN-CAR-Introduced Cells 8-1: Lentivirus Transduction Transduction was performed a total of twice. Anti-CD3 (1 μg/mL) and anti-CD28 (3 μg/mL) antibodies were prepared at a predetermined concentration in 5 mL of DPBS, followed by vortexing. Then, each antibody was coated onto a 24-well plate at a density of 500 μl/well, and stored in a refrigerator at 4° C. overnight. Next day, PBMC (human primary PBMC) was dissolved in 9 mL of T cell culture medium (10% FBS+RPMI1640+200 IU IL-2), and centrifuged at 1,500 rpm for 5 minutes. Thereafter, the supernatant was removed, and the resultant was resuspended in 1 mL of a culture medium, followed by cell counting. After dilution to 1×10⁶ cells/mL, cells were seeded in the antibody-coated 24-well plate, and then incubated in a CO₂ incubator at 37° C. After 3 days, all PBMC cells were harvested. For lentivirus infection, of 5 in 5×10⁵ of lentivirus was adjusted at multiple of infection (MOI) of 5, and 10 μg/mL of protamine sulfate was added to cells, which were then seeded in a new 24-well plate (a). The 24-well plate was centrifuged at 300 g, 32° C. for 90 minutes, and then incubated in a CO₂ incubator at 37° C. (b). Next day, all T cells were harvested and the above (a) and (b) were performed once more. Then, all T cells were harvested and centrifuged at 1,500 rpm for 5 minutes to remove the supernatant, and the T cells were resuspended in the culture medium and cultured again.

8-2: Examination of Anti-MSLN-CAR Expression

The presence or absence of CAR expression was examined in T cells into which the anti-MSLN-CAR prepared in Example 8-1 was introduced. Five days after the completion of lentivirus transduction of T cells, a portion of anti-MSLN-CAR-T cells were harvested, and biotin-MSLN (Acrobiosystems or Biolegend) was added thereto, followed by incubation on ice for 20 minutes. Then, cells were washed, and 1 µL of PE-anti-biotin was added, followed by incubation on ice for 20 minutes. After washing the cells, an expression rate of CAR was examined using FACS Canto II (BD). Further, the expression of finally differentiated T cells (CD3) was analyzed by FACS while incubating anti-MSLN-CAR-T for 14 days, and a percentage of CD4+ and CD8+ T cells in CD3-positive T cells was measured. The results are shown in Table 11 below and FIGS. 10 and 11.

TABLE 11

| Round of transduction | Clone | CD3-positive T cells % | CAR expression % |
|---|---|---|---|
| 1$^{st}$ round | CD19 (FMC63) | 93.3% | 29.2% |
| 1$^{st}$ round | MSLN34 CAR scFv | 94.3% | 22.4% |
| 1$^{st}$ round | MSLN38 CAR scFv | 97.3% | 8.99% |
| 2$^{nd}$ round | CD19(FMC63) | 91.2% | 30.9% |
| 2$^{nd}$ round | MSLN34 CAR scFv | 92.9% | 27.2% |
| 2$^{nd}$ round | MSLN38 CAR scFv | 91.3% | 27.9% |

Figure 10:
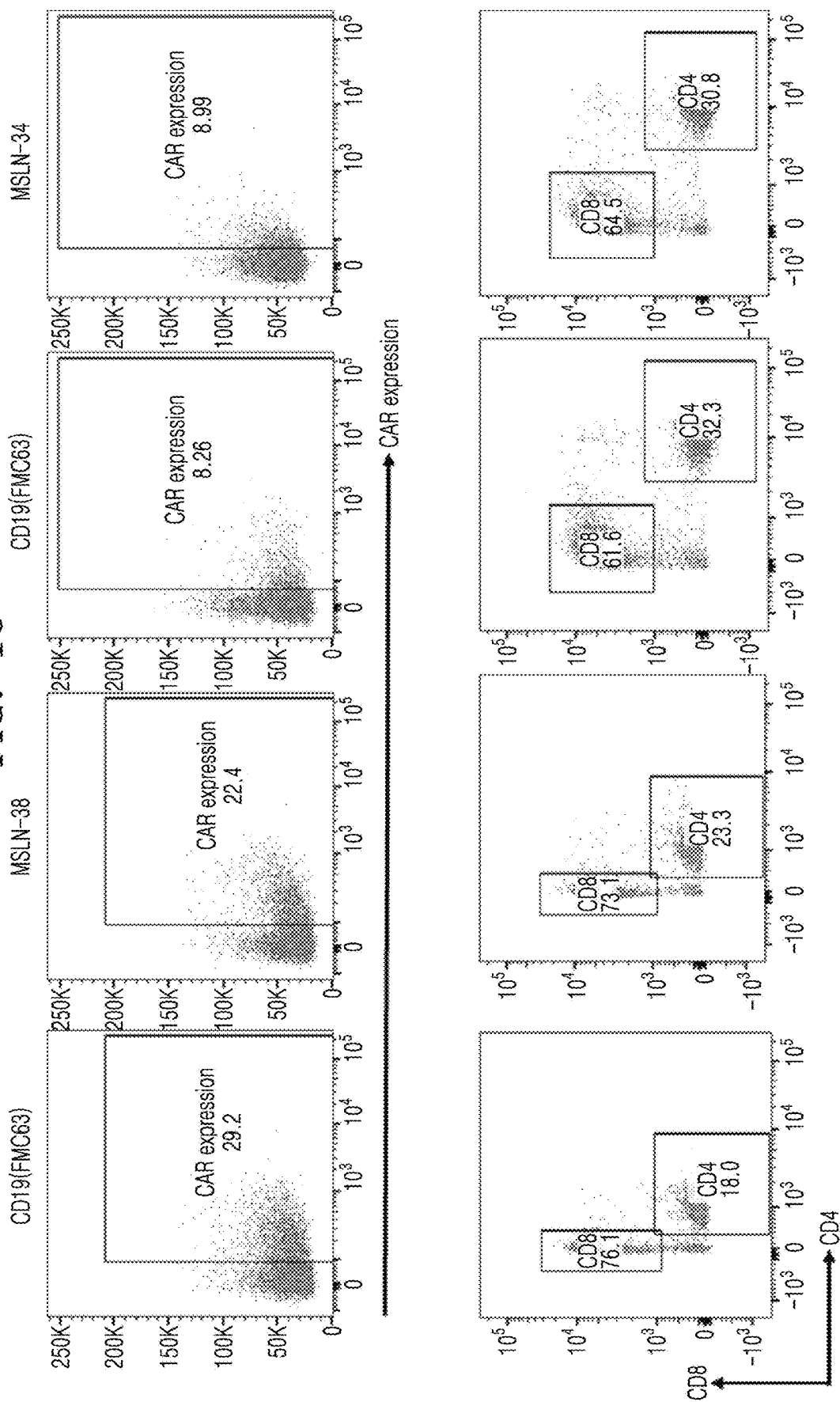
FIG. 10 shows results of examining CAR expression in anti-MSLN-CAR-introduced T cells and measuring a percentage of CD4+ and CD8+ T cells in CD3-positive T cells, after a first round of transduction.
Figure 11:
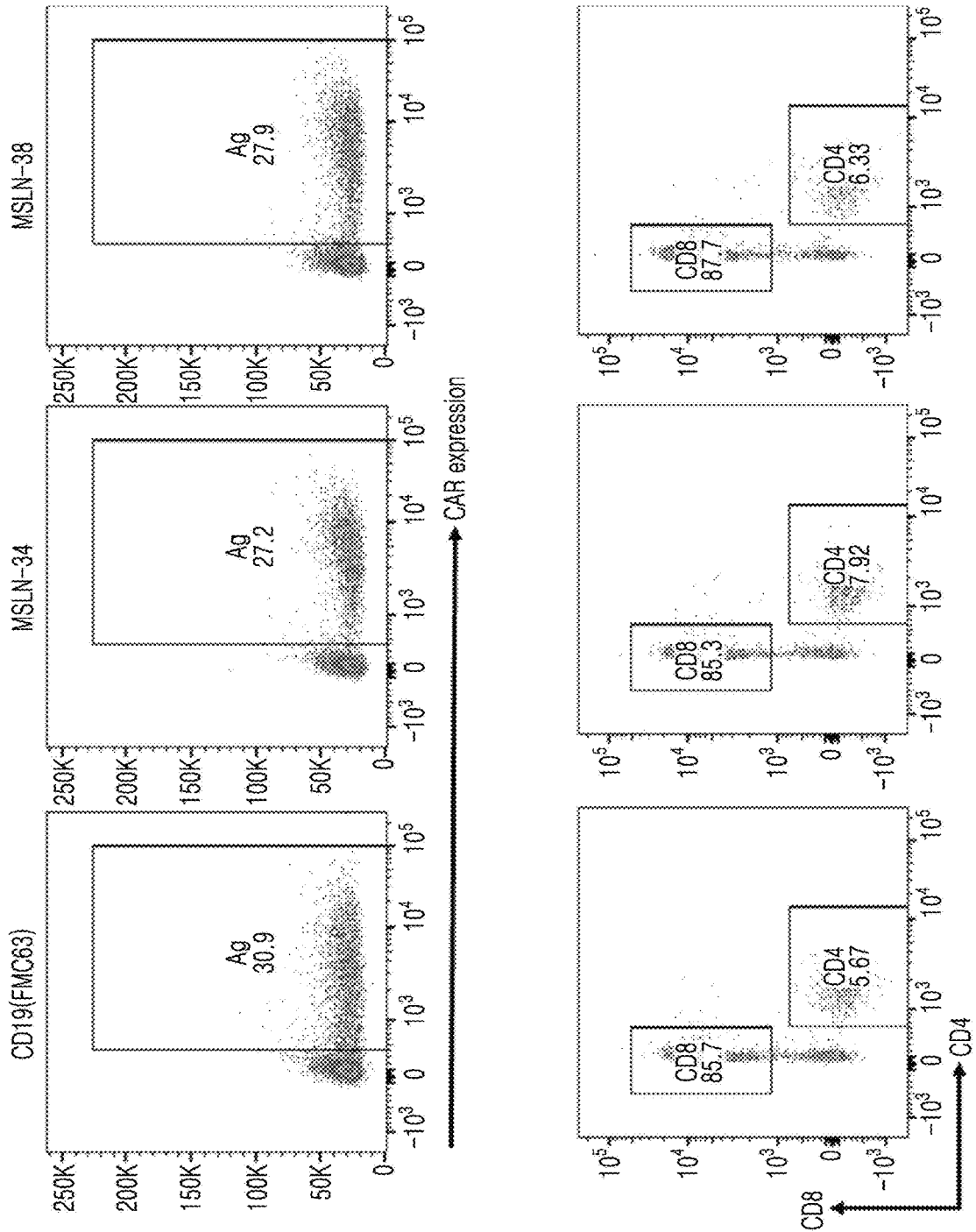
FIG. 11 shows results of examining CAR expression in anti-MSLN-CAR-introduced T cells and measuring a percentage of CD4+ and CD8+ T cells in CD3-positive T cells, after a second round of transduction.

As shown in FIGS. 10 and 11, as a result of the 1$^{st}$ round of transduction, a percentage of CD4+:CD8+ was 20%:70% on average, and as a result of the 2$^{nd}$ round of transduction, a percentage of CD4+:CD8+ was 10%:80%.

Example 9: Examination of Cell-Killing Effects of Anti-MSLN-CAR-T Cells

Cell-killing effects on cancer cells were examined using the anti-MSLN-CAR-T cells prepared in Example 8 by a Calcein-AM assay.

Figure 12:
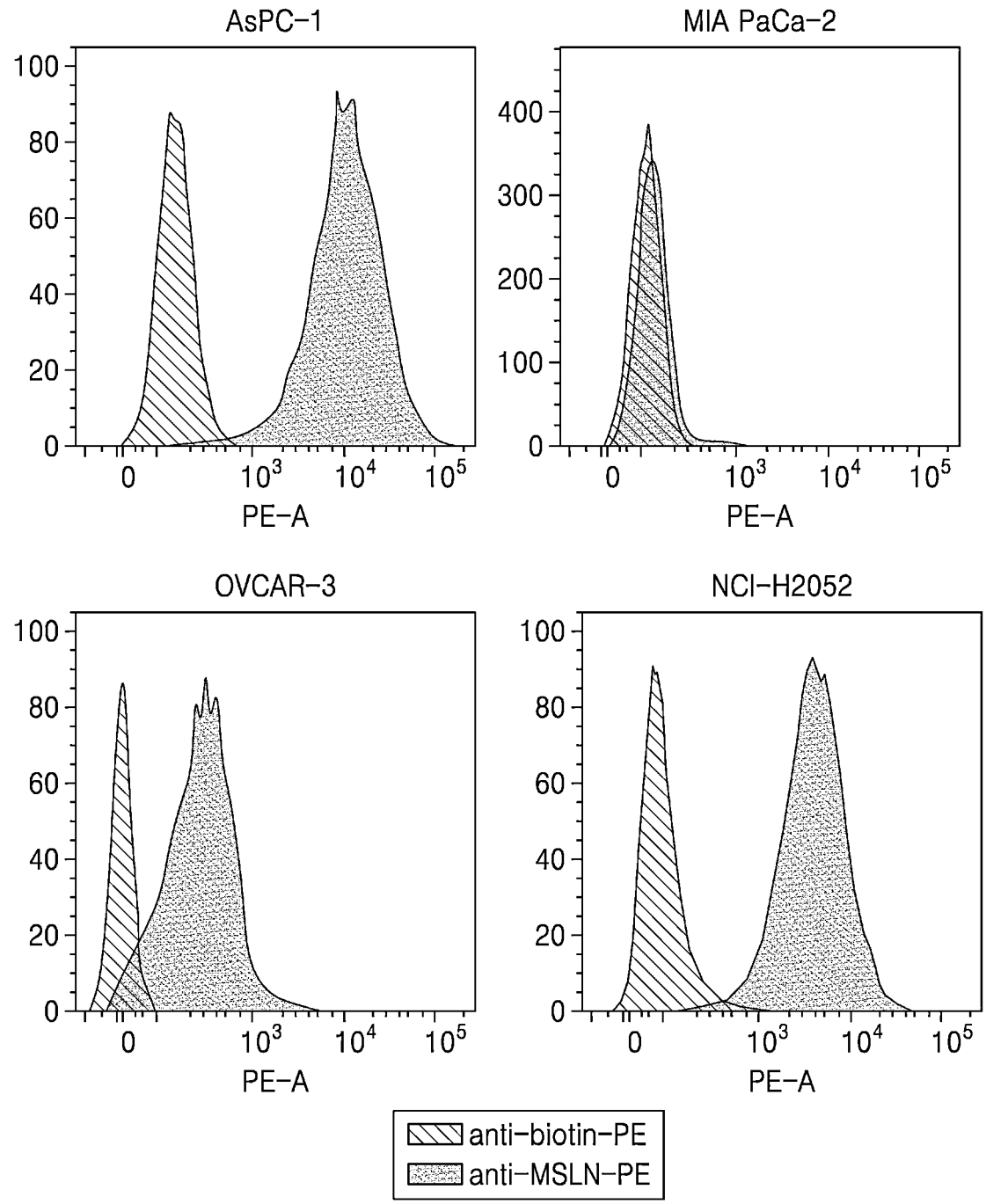
FIG. 12 shows results of examining cell killing effects of anti-MSLN-CAR-introduced T cells using various cancer cell lines.

First, to examine MSLN expression levels of various cancer cell lines (AsPC-1, MIA PaCa-2, NCI-H2052, and OVCAR-3), a portion of the cells was taken during culture, and bound with biotin-anti-MSLN antibodies, followed by FACS analysis. As a result, MSLN expression was observed all in AsPC-1 which is a pancreatic cancer cell line, OVCAR-3 which is an ovarian cancer cell line, and NCI-H2052 which is a malignant pleural mesothelioma cell line. However, MIA PaCa-2 which is a pancreatic cancer cell line showed significantly low MSLN expression, as compared with other cancer cell lines (FIG. 12).

The cancer cell lines (AsPC-1, MIA PaCa-2, NCI-H2052, and OVCAR-3) were resuspended in each culture medium at a density of 1×10$^6$ cells/mL, 5 µL of calcein-AM (1 mg/mL) was added, and mixed well, followed by incubation for 1 hour in a 37° C. incubator. CD19-CAR-T cells and anti-MSLN-CAR-T cells which are effector cells were prepared by diluting at various E:T (effector cell:target cell) ratios while adding the cell culture medium. 1 hour after calcein-AM staining of the cancer cell lines, centrifugation was performed at 1,200 rpm for 5 minutes, followed by washing and resuspending by adding 10 mL of culture medium. Then, 100 µL (1×10$^4$ cells/100 µL) of the stained cancer cell line was seeded in a 96-well round plate, and 100 µL of effector cells were seeded thereon. As a control group, a calcein-AM-stained cancer cell line treated with only 100 µL of culture medium (spontaneous value) or treated with 2% Triton X-100 (maximum value) was used. The 96-well round plate was centrifuged at 100 g for 1 minute, and then incubated for 4 hours in a 37° C. incubator. After 4 hours, the cells in the well were mixed five times with a pipette, centrifuged at 100 g for 5 minutes, and 100 µL of only the supernatant was taken and transferred to an assay 96-well plate. Calcein emission was measured at an excitation wavelength of 485 nm and an emission wavelength of 535 nm with a fluorescent microplate reader using the 96-well plate containing the supernatant. The cell killing effect was calculated using the measured values according to the following equation. The results are shown in FIGS. 13 to 15.

Cell killing effect (%)=(Experimental release−Spontaneous release)/(Maximum release−Spontaneous release)×100     [Equation 2]

Figure 13:
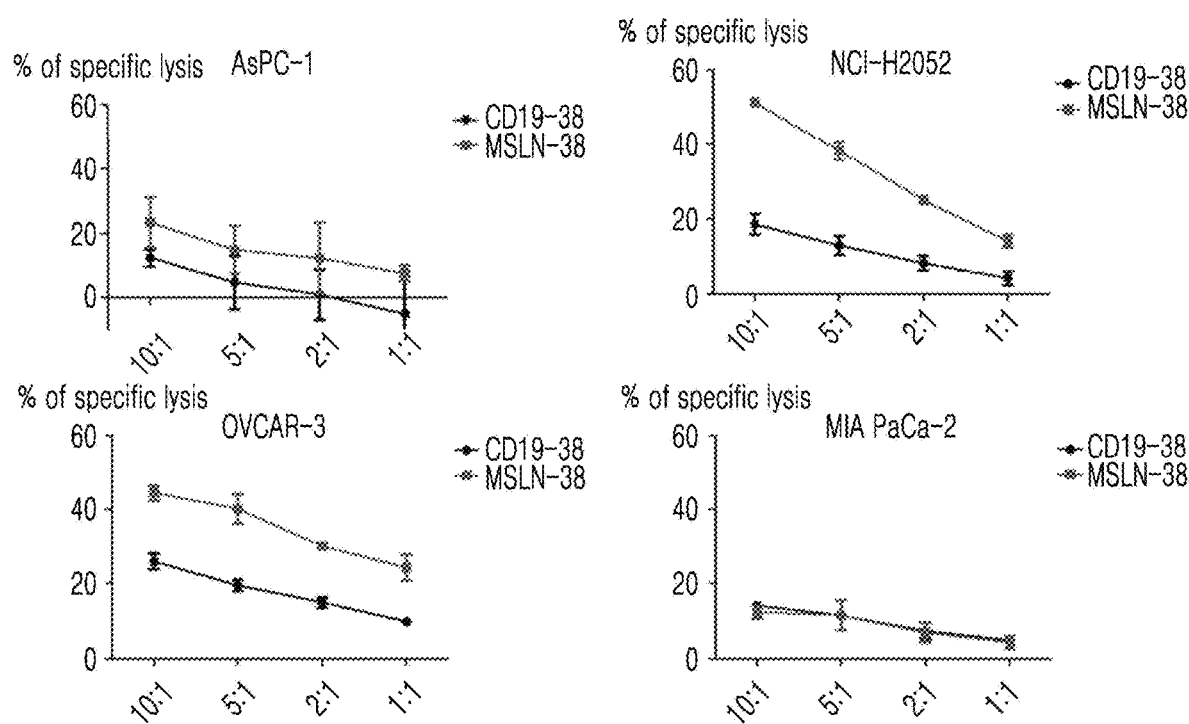
FIGS. 13 to 16 show results of examining cell killing effects of anti-MSLN34-CAR-T and anti-MSLN38-CAR-T.
Figure 14:
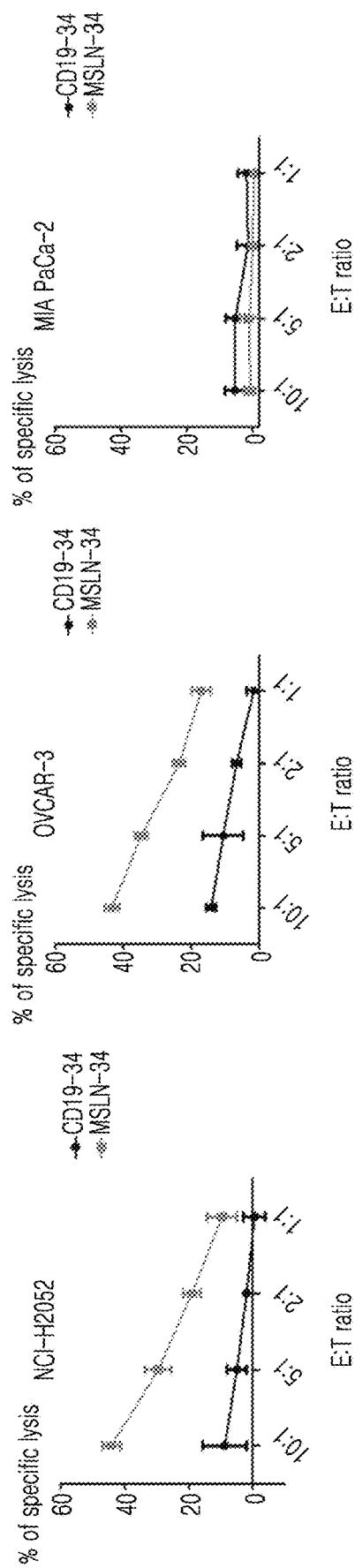
Figure 15:
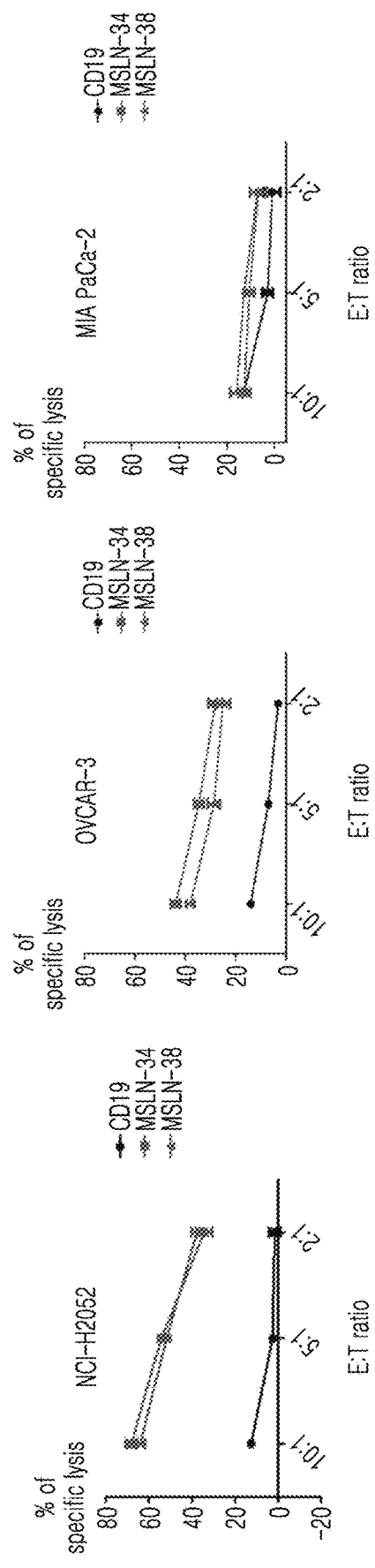

As shown in FIGS. 13 to 15, both anti-MSLN34-CAR-T and anti-MSLN38-CAR-T showed a significant antigen-specific cell-killing effect on the ovarian cancer cell line OVCAR-3 and the malignant pleural mesothelioma cell line NCI-H2052, in which high MSLN expression was confirmed, as compared with the negative control CD19 (FMC63)-CAR-T. However, both anti-MSLN34-CAR-T and anti-MSLN38-CAR-T showed no specific cell-killing effect on MIA PaCa-2 which is a cancer cell line showing low MSLN expression, as compared with the negative control. These results confirmed that the cell-killing effect of the anti-MSLN-CAR-T cells according to one aspect is specific to mesothelin expressed in cancer cells.

Figure 16:
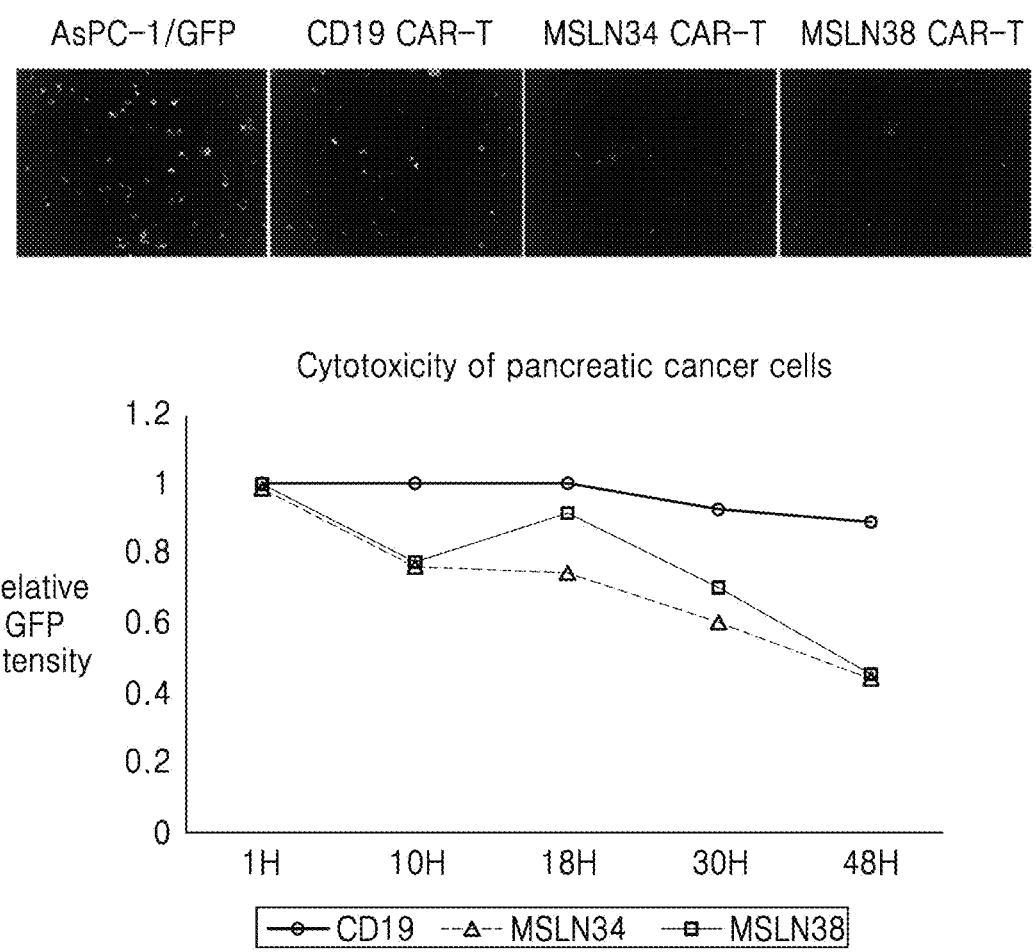
Figure 17A:
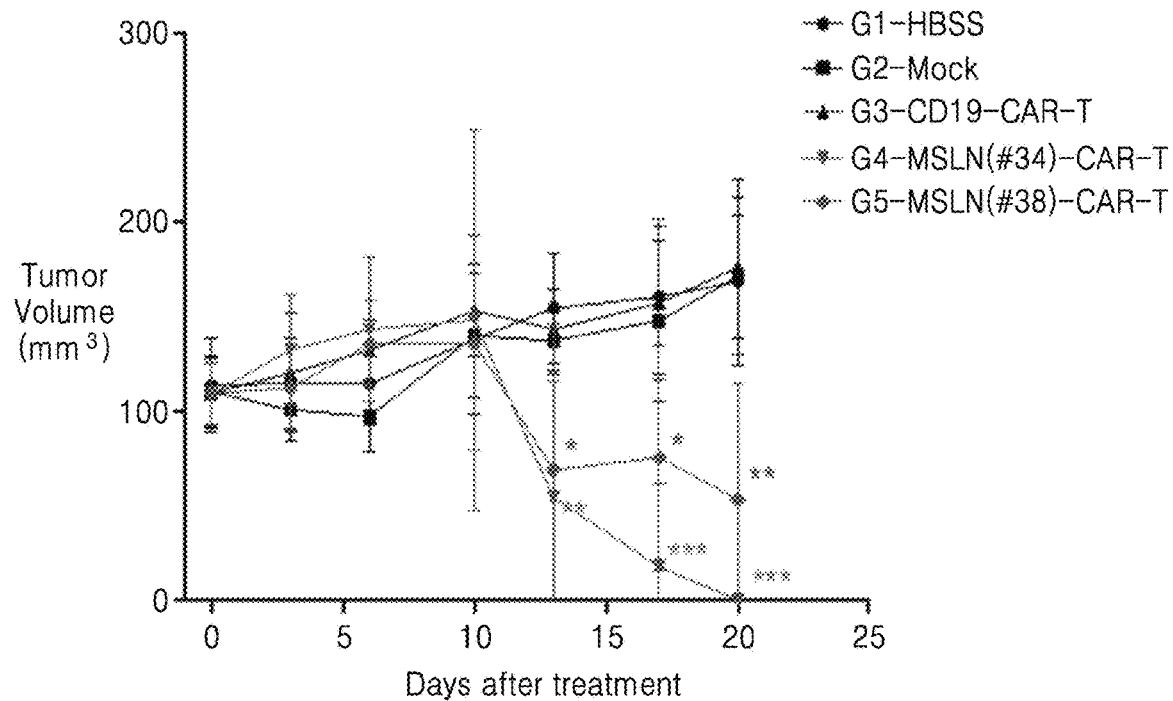
FIG. 17 shows results of examining cancer cell-killing efficacy and body weight changes in mesothelioma animal models due to anti-MSLN34-CAR-T and anti-MSLN38-CAR-T (A: change in tumor volume, B: change in body weight, C: change in tumor weight)
Figure 17B:
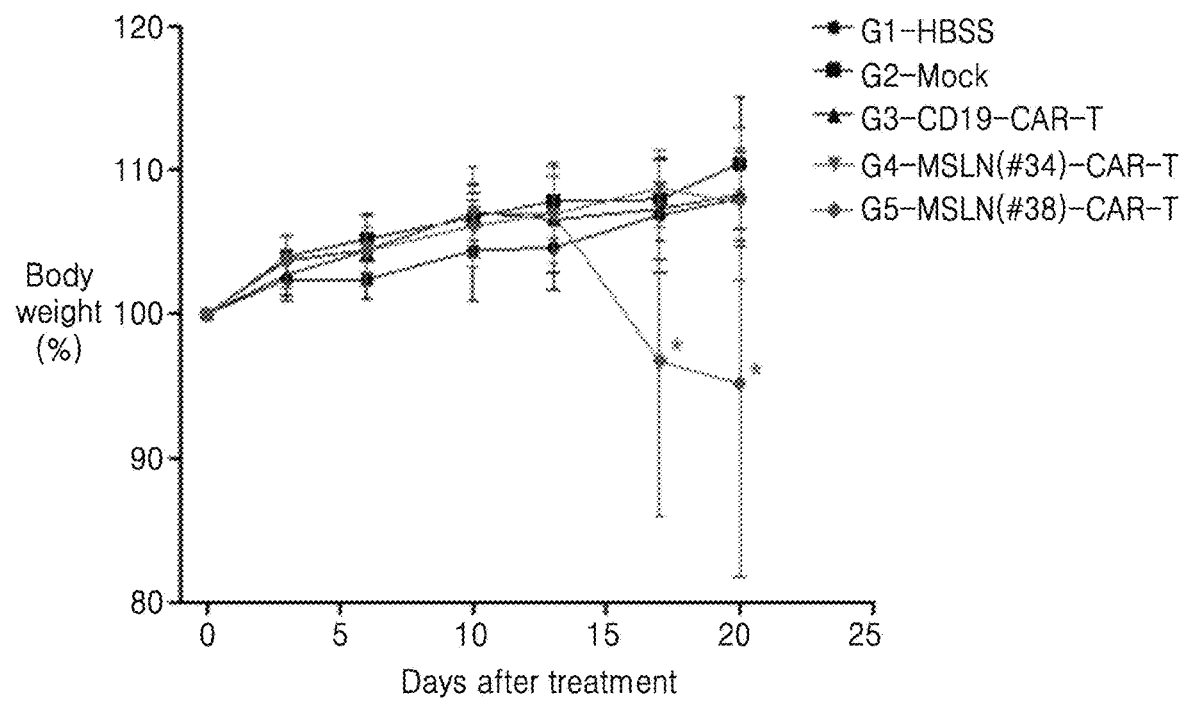
Figure 17C:
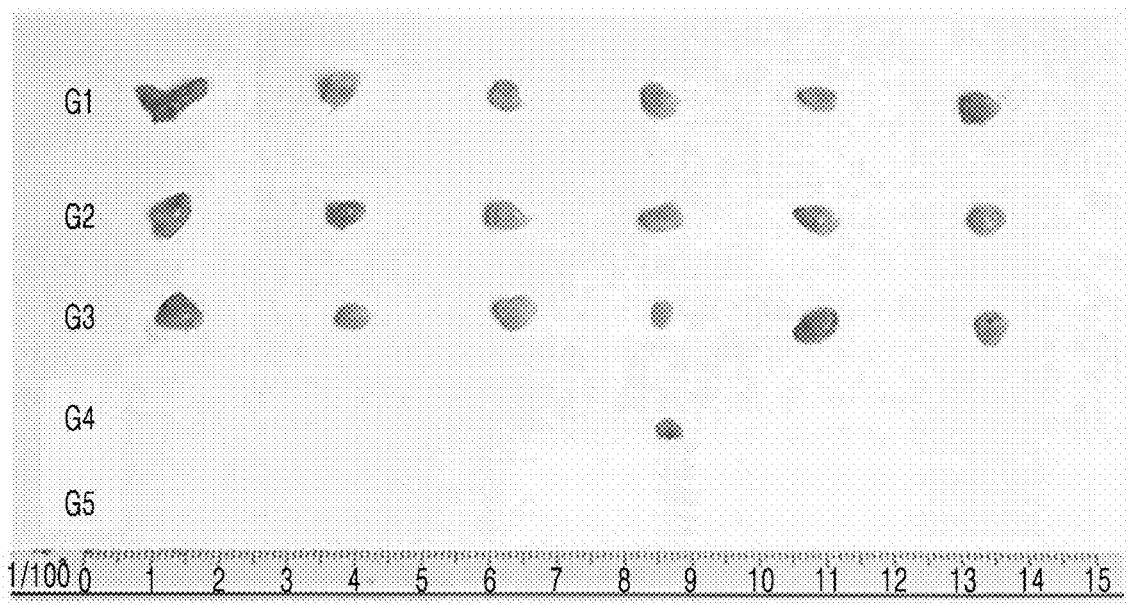
Figure 17C:
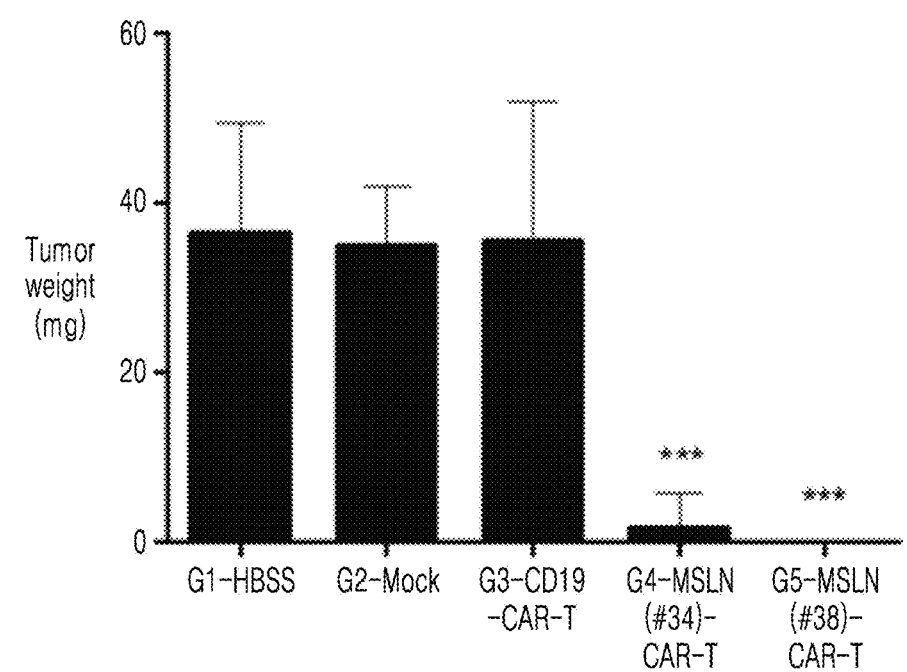
Figure 18A:
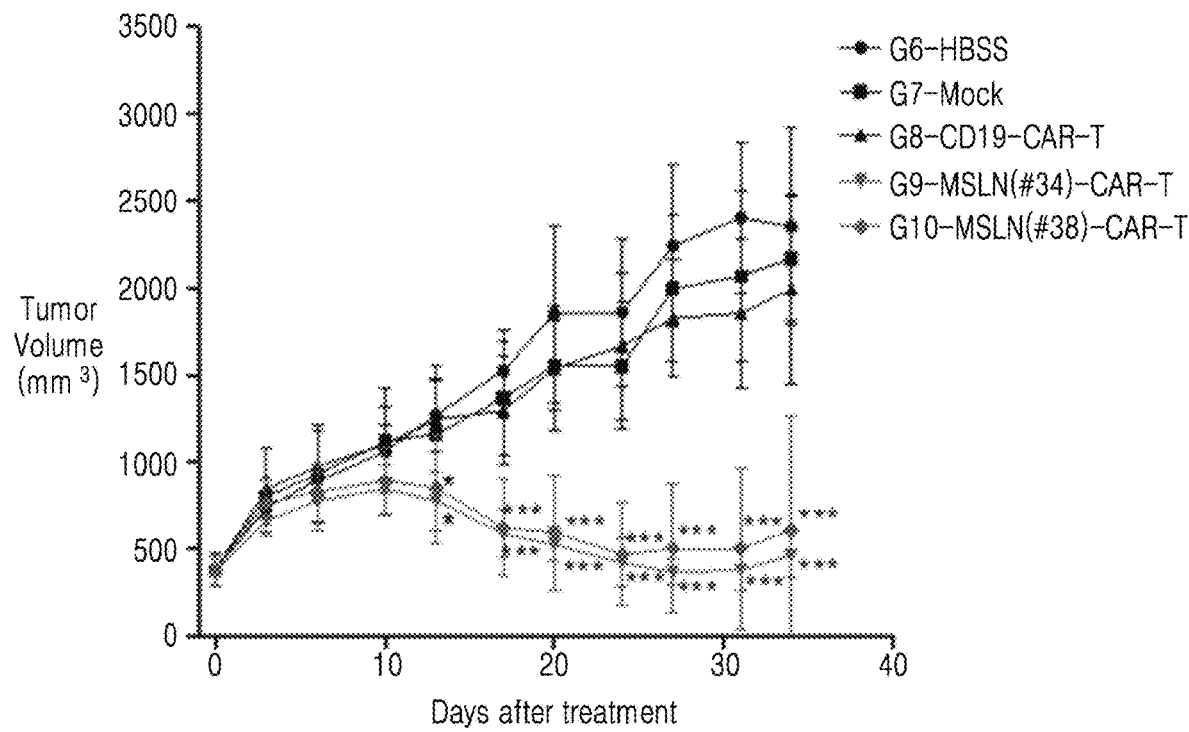
FIG. 18 shows results of examining cancer cell-killing efficacy and body weight changes in pancreatic cancer animal models due to anti-MSLN34-CAR-T and anti-MSLN38-CAR-T (A: change in tumor volume, B: change in body weight, C: change in tumor weight).
Figure 18B:
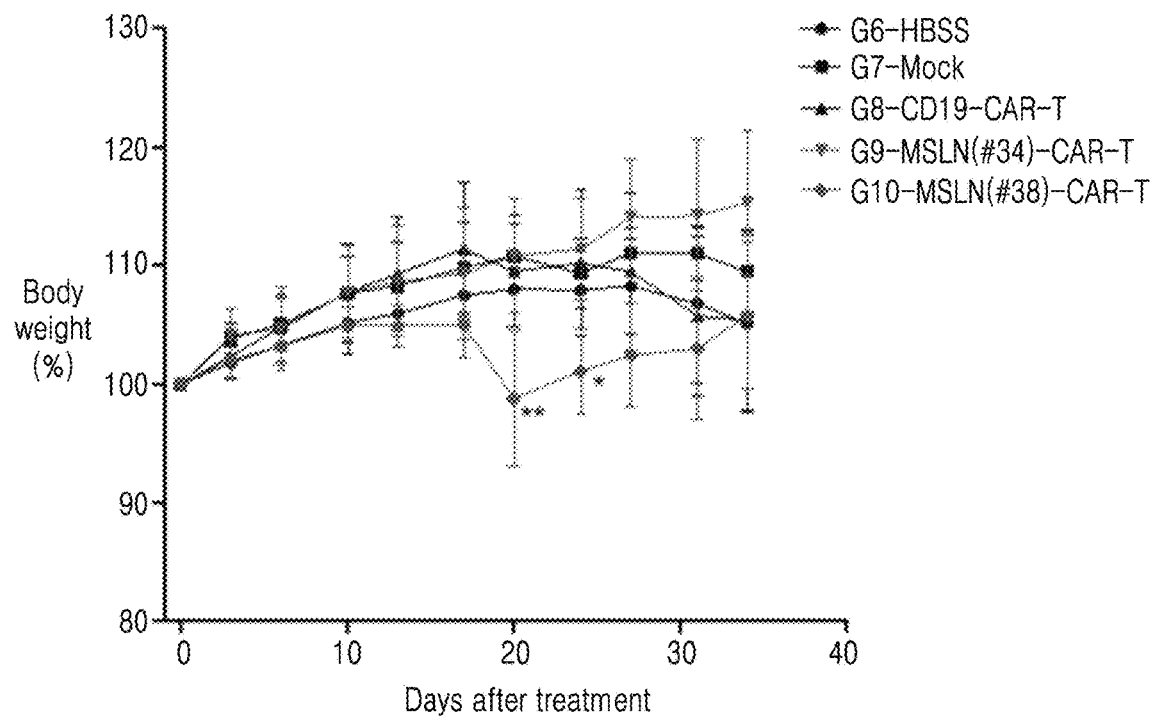
Figure 18C:
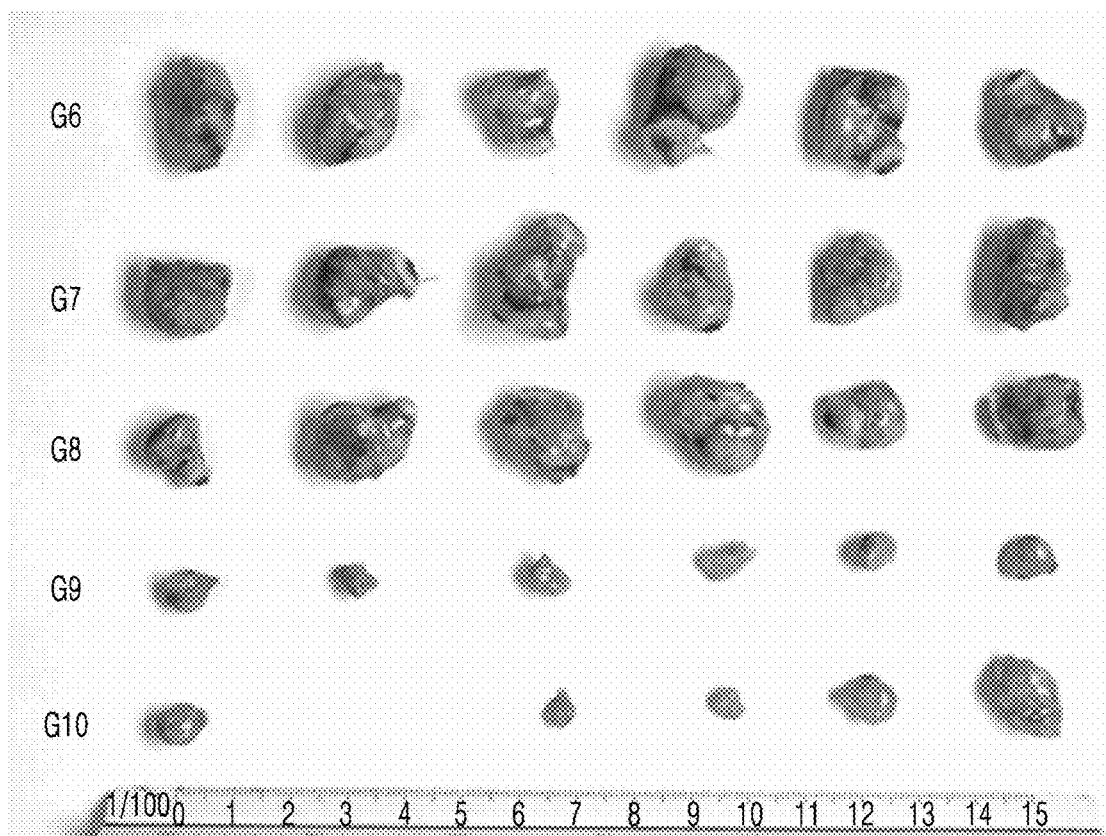
Figure 18C:
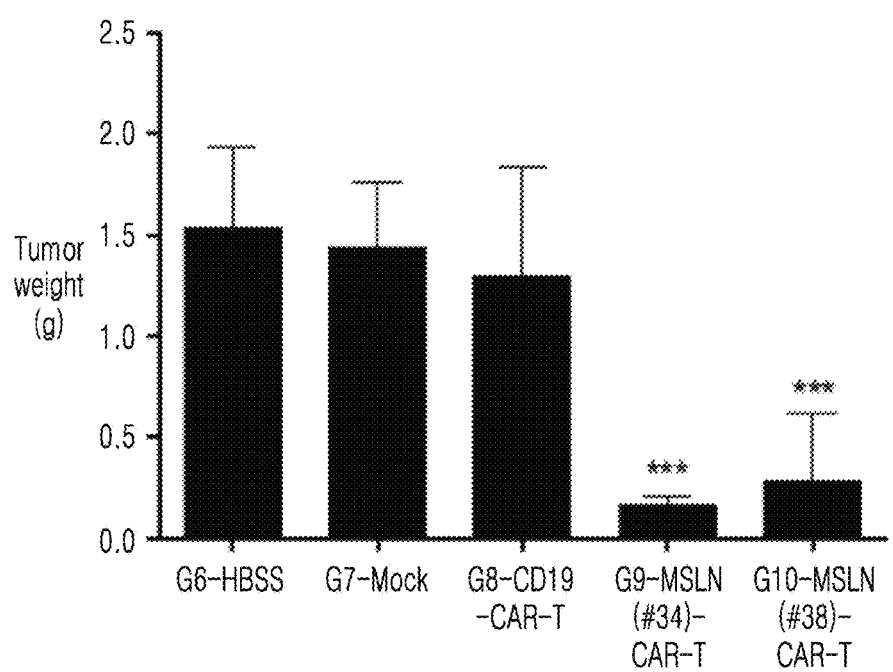

The cell killing effects on cancer cells were also examined using the anti-MSLN-CAR-T cells prepared in Example 8 and a cancer cell line expressing green fluorescent protein (GFP). AsPC-1 which is a GFP-expressing pancreatic cancer cell line was resuspended in a culture medium at a density of 1×10$^6$ cells/mL, and incubated. Then, the effector cells, CD19-CAR-T cells and anti-MSLN-CAR-T cells, were added to the cell culture medium, and co-cultured at an E:T ratio of 10:1. Results of measuring GFP up to 48 hours in real-time using an incucyte are shown in FIG. 16. As shown in FIG. 16, it was confirmed that the cell killing effect on the pancreatic cancer cell line AsPC-1 was observed according to the treatment with the anti-MSLN-CAR-T cells according to an aspect.

Example 10: Examination of Cancer Cell-Killing Effect of Anti-MSLN-CAR-T Cells, Based on Tumor Animal Model Based on the cell-killing effect of anti-MSLN-CAR-T cells on cancer cells, as confirmed in Example 9, a tumor animal model was constructed and the tumor killing ability was examined.

In this experiment, 5-week-old male NOG (NOD/Shi-scid/IL-2Rγnull) mice were used. When the animals were supplied, the inspection and quarantine of the animals was conducted with reference to the health monitoring report of the test system provided by the supplier. After acclimatization for a week, the experiment was conducted. The breeding environment for this experiment was as follows: a temperature of 22° C.±2° C., relative humidity of 50%±10%, ventilation of 10 times to 20 times/hr, lighting time of 12 hours (light-up at 8 am~light-out at 8 pm), and illuminance of 150 Lux to 300 Lux. After autoclaving chip-type bedding materials (121° C., sterilization time of 20 minutes, drying time of 5 minutes), an appropriate amount of the chip-type bedding materials was placed in a polycarbonate breeding box (W 278 (mm)×L 420 (mm)×H 230 (mm)) to breed the mice. A feed supplied during the experiment was a solid feed for laboratory animals, sterilized by irradiation (+40 RMM-SP-10, U8239G10R, SAFE-DIETS, France), and RO water in a water bottle was sterilized by autoclaving, and mice were allowed free access to the water.

Cells used in pancreatic cancer and mesothelioma animal models were tested for *Mycoplasma pneumoniae*, Murine coronavirus (Mouse hepatitis virus, MHV), and Murine respirovirus (Sendai virus, SeV), and the cells were confirmed to be negative before use. The compositions of transplanted cancer cells and CAR-T cells and test groups are shown in Table 12 below.

TABLE 12

| Group | N (number) | Cell line (cells/mouse) | Administration Material | Administration Route | Dose (CAR-Ts/mouse) | Volume |
|---|---|---|---|---|---|---|
| G1 | 6 | AsPC-1 | HBSS | I.V | — | 200 uL |
| G2 | 6 | (5 × 10$^6$) | Mock | | — | |
| G3 | 6 | | CD19-CAR-T | | 5 × 10$^6$ | |
| G4 | 6 | | Anti-MSLN34-CAR-T | | 5 × 10$^6$ | |
| G5 | 6 | | Anti-MSLN38-CAR-T | | 5 × 10$^6$ | |
| G6 | 6 | NCI-H2052 | HBSS | | — | |
| G7 | 6 | (1 × 10$^7$) | Mock | | — | |
| G8 | 6 | | CD19-CAR-T | | 5 × 10$^6$ | |
| G9 | 6 | | Anti-MSLN34-CAR-T | | 5 × 10$^6$ | |
| G10 | 6 | | Anti-MSLN38-CAR-T | | 5 × 10$^6$ | |

Concentrations of the cells were adjusted using PBS, and each 200 uL thereof was subcutaneously transplanted into mice. Groups were divided according to tumor size by randomization. Individual identification was performed using an ear-punch method during the experiment period, and an identification card for each group was attached to the breeding box.

After dividing the experimental groups, anti-MSLN-CAR-T cells were administered once via the tail vein, and the body weight and tumor size of the experimental groups were measured twice a week from the beginning of administration. Based on the body weight on the beginning day of administration, changes in the body weight were observed until the end of the experiment. Body weight gain or loss (%) was calculated using the following equation.

Body weight gain or loss (%)=(Body weight/Body weight on day 0)×100 [Equation 3]

The tumor volume (mm$^3$) was calculated using the following equation after measuring the short axis (A) and long axis (B) of the tumor using calipers.

Tumor volume (mm$^3$)=½×[{$A$ (mm)}$^2$×$B$ (mm)] [Equation 4]

After the last measurement, the body weight and tumor volume were statistically analyzed using a post-hoc Dunnett's test of one-way ANOVA by comparing HBSS-administered groups and anti-MSLN-CAR-T-administered groups, each for pancreatic cancer and mesothelioma (*:p<0.05, :p<0.01, *:p<0.001).

As a result of validation of the tumor-killing ability of anti-MSLN-CAR-T cells in the mesothelioma (NCI-H2052) model, no tumors were observed in all animals of the anti-MSLN34-CAR-T-administered groups and the anti-MSLN38-CAR-T-administered groups, except for one individual (G4-4). As compared with the HBSS-administered group, the tumor size was significantly reduced in the anti-MSLN34-CAR-T-administered groups and the anti-MSLN38-CAR-T-administered groups from the 13$^{th}$ day of administration (p<0.05). As compared with the control group (G1, HBSS-administered group), the anti-MSLN38-CAR-T-administered group showed weight loss (p<0.05) and convulsions, and two mice died on the 20$^{th}$ day after administration. The results are shown in FIG. 17.

As a result of validation of the tumor-killing ability of anti-MSLN-CAR-T cells in the pancreatic cancer (AsPC-1) model, the tumor size was significantly reduced in the anti-MSLN34-CAR-T-administered groups and the anti-MSLN38-CAR-T-administered groups from the 13$^{th}$ day of administration (p<0.05), as compared with the HBSS-administered group. At autopsy, the tumor weight decreased in both groups at the same time (p<0.05). As compared with the control group (G6, HBSS-administered group), the anti-MSLN38-CAR-T-administered group showed weight loss (p<0.05) and convulsions, and one mouse died on the 34$^{th}$ day after administration. The results are shown in FIG. 18.

The above results taken together, it was confirmed that both anti-MSLN34-CAR-T and anti-MSLN38-CAR-T show the cancer cell-killing effects on cancer cells of both pancreatic cancer and mesothelioma as well as on animal models thereof.

The above description is for illustrating, and it will be understood by those skilled in the art that the present disclosure may be implemented in a different specific form without changing the technical spirit or essential characteristics thereof. Therefore, it should be understood that the embodiments described herein are not limitative, but illustrative in all aspects.

The invention claimed is:

1. An anti-mesothelin antibody or antigen-binding fragment thereof, comprising a heavy chain variable region comprising the following heavy chain CDRs and a light chain variable region comprising the following light chain CDRs:

a heavy chain CDR1 comprising an amino acid sequence consisting of SEQ ID NO: 1, a heavy chain CDR2 comprising an amino acid sequence consisting of SEQ ID NO: 2, a heavy chain CDR3 comprising an amino acid sequence consisting of SEQ ID NO: 3, and a light chain CDR1 comprising an amino acid sequence consisting of SEQ ID NO: 4, a light chain CDR2 comprising an amino acid sequence consisting of SEQ ID NO: 5, and a light chain CDR3 comprising an amino acid sequence consisting of SEQ ID NO: 6; or a heavy chain CDR1 comprising an amino acid sequence consisting of SEQ ID NO: 13, a heavy chain CDR2 comprising an amino acid sequence consisting of SEQ ID NO: 14, a heavy chain CDR3 comprising an amino acid sequence consisting of SEQ ID NO: 15, and a light chain CDR1 comprising an amino acid sequence consisting of SEQ ID NO: 16, a light chain CDR2 comprising an amino acid sequence consisting of SEQ ID NO: 17, and a light chain CDR3 comprising an amino acid sequence consisting of SEQ ID NO: 18.

2. The anti-mesothelin antibody or antigen-binding fragment thereof according to claim 1, comprising:

a heavy chain variable region comprising an amino acid sequence consisting of SEQ ID NO: 19 or 23.

3. The anti-mesothelin antibody or antigen-binding fragment thereof according to claim 1, comprising: a light chain variable region comprising an amino acid sequence consisting of SEQ ID NO: 20 or 24.

4. The anti-mesothelin antibody or antigen-binding fragment thereof according to claim 1, comprising: a heavy chain variable region comprising an amino acid sequence consisting of SEQ ID NO: 19; and a light chain variable region comprising an amino acid sequence consisting of SEQ ID NO: 20.

5. The anti-mesothelin antibody or antigen-binding fragment thereof according to claim 1, comprising: a heavy chain variable region comprising an amino acid sequence consisting of SEQ ID NO: 23; and a light chain variable region comprising an amino acid sequence consisting of SEQ ID NO: 24.

6. An isolated nucleic acid encoding the anti-mesothelin antibody or antigen-binding fragment thereof according to any one of claims 1 to 5.

7. A vector comprising the isolated nucleic acid according to claim 6.

8. An isolated host cell transformed with the vector according to claim 7.

9. A method of preparing an anti-mesothelin antibody, the method comprising expressing the antibody by culturing the host cell according to claim 8.

10. A chimeric antigen receptor comprising an antigen-binding domain, a hinge domain, a transmembrane domain, and an intracellular signaling domain,
wherein the antigen-binding domain is an anti-mesothelin antibody or antigen-binding fragment thereof comprising a heavy chain variable region comprising the following heavy chain CDRs and a light chain variable region comprising the following light chain CDRs:
a heavy chain CDR1 comprising an amino acid sequence consisting of SEQ ID NO: 1, a heavy chain CDR2 comprising an amino acid sequence consisting of SEQ ID NO: 2, a heavy chain CDR3 comprising an amino acid sequence consisting of SEQ ID NO: 3, and a light chain CDR1 comprising an amino acid sequence consisting of SEQ ID NO: 4, a light chain CDR2 comprising an amino acid sequence consisting of SEQ ID NO: 5, and a light chain CDR3 comprising an amino acid sequence consisting of SEQ ID NO: 6; or
a heavy chain CDR1 comprising an amino acid sequence consisting of SEQ ID NO: 13, a heavy chain CDR2 comprising an amino acid sequence consisting of SEQ ID NO: 14, a heavy chain CDR3 comprising an amino acid sequence consisting of SEQ ID NO: 15, and a light chain CDR1 comprising an amino acid sequence consisting of SEQ ID NO: 16, a light chain CDR2 comprising an amino acid sequence consisting of SEQ ID NO: 17, and a light chain CDR3 comprising an amino acid sequence consisting of SEQ ID NO: 18.

11. The chimeric antigen receptor according to claim 10, wherein the antigen-binding domain is an anti-mesothelin antibody or antigen-binding fragment thereof comprising: a heavy chain variable region comprising an amino acid sequence consisting of SEQ ID NO: 19; and a light chain variable region comprising an amino acid sequence consisting of SEQ ID NO: 20.

12. The chimeric antigen receptor according to claim 10, wherein the antigen-binding domain is an anti-mesothelin antibody or antigen-binding fragment thereof comprising: a heavy chain variable region comprising an amino acid sequence consisting of SEQ ID NO: 23; and a light chain variable region comprising an amino acid sequence consisting of SEQ ID NO: 24.

13. The chimeric antigen receptor according to claim 10, wherein the antigen-binding fragment is a single chain variable fragment (scFv).

14. A polynucleotide encoding the chimeric antigen receptor according to claim 10.

15. The polynucleotide according to claim 14, wherein the polynucleotide comprises a base sequence consisting of SEQ ID NO: 26 or 27.

16. A vector comprising the polynucleotide according to claim 14.

17. An isolated cell transformed with the vector according to claim 16.

18. The isolated cell according to claim 17, wherein the cell is a T cell, an NK cell, an NKT cell, or a gamma delta (γδ) T cell.

19. A pharmaceutical composition comprising the isolated cell according to claim 18, and a pharmaceutically acceptable carrier.

* * * * *

SEQUENCE LISTING

```
<160> NUMBER OF SEQ ID NOS: 40

<210> SEQ ID NO 1
<211> LENGTH: 5
<212> TYPE: PRT
<213> ORGANISM: Artificial
<220> FEATURE:
<223> OTHER INFORMATION: MSLN34 HCDR1

<400> SEQUENCE: 1

Asp Tyr Gly Met His
1               5

<210> SEQ ID NO 2
<211> LENGTH: 17
```

```
<212> TYPE: PRT
<213> ORGANISM: Artificial
<220> FEATURE:
<223> OTHER INFORMATION: MSLN34 HCDR2

<400> SEQUENCE: 2

Ser Ile Tyr Gly Ser Gly Gly His Thr Gly Tyr Ala Asp Ser Val Lys
1               5                   10                  15

Gly

<210> SEQ ID NO 3
<211> LENGTH: 12
<212> TYPE: PRT
<213> ORGANISM: Artificial
<220> FEATURE:
<223> OTHER INFORMATION: MSLN34 HCDR3

<400> SEQUENCE: 3

Gln His Ala Tyr Arg Tyr Ser Tyr Ala Phe Asp Val
1               5                   10

<210> SEQ ID NO 4
<211> LENGTH: 11
<212> TYPE: PRT
<213> ORGANISM: Artificial
<220> FEATURE:
<223> OTHER INFORMATION: MSLN34 LCDR1

<400> SEQUENCE: 4

Arg Ala Ser Gln Ser Ile Ser Asn Trp Leu Asn
1               5                   10

<210> SEQ ID NO 5
<211> LENGTH: 7
<212> TYPE: PRT
<213> ORGANISM: Artificial
<220> FEATURE:
<223> OTHER INFORMATION: MSLN34 LCDR2

<400> SEQUENCE: 5

Ala Thr Ser Ser Leu Gln Ser
1               5

<210> SEQ ID NO 6
<211> LENGTH: 9
<212> TYPE: PRT
<213> ORGANISM: Artificial
<220> FEATURE:
<223> OTHER INFORMATION: MSLN34 LCDR3

<400> SEQUENCE: 6

Gln Gln Ser Tyr Ser Phe Pro Phe Thr
1               5

<210> SEQ ID NO 7
<211> LENGTH: 5
<212> TYPE: PRT
<213> ORGANISM: Artificial
<220> FEATURE:
<223> OTHER INFORMATION: MSLN37 HCDR1

<400> SEQUENCE: 7

Ser Tyr Ala Met His
1               5

<210> SEQ ID NO 8
```

```
<211> LENGTH: 17
<212> TYPE: PRT
<213> ORGANISM: Artificial
<220> FEATURE:
<223> OTHER INFORMATION: MSLN37 HCDR2

<400> SEQUENCE: 8

Gly Ile Ser Gly Ser Gly Gly Thr Thr Tyr Tyr Ala Asp Ser Val Lys
1               5                   10                  15
Gly

<210> SEQ ID NO 9
<211> LENGTH: 12
<212> TYPE: PRT
<213> ORGANISM: Artificial
<220> FEATURE:
<223> OTHER INFORMATION: MSLN37 HCDR3

<400> SEQUENCE: 9

Glu Val Glu Gly Gln Ser Gln Glu Tyr Phe Asp Ile
1               5                   10

<210> SEQ ID NO 10
<211> LENGTH: 11
<212> TYPE: PRT
<213> ORGANISM: Artificial
<220> FEATURE:
<223> OTHER INFORMATION: MSLN37 LCDR1

<400> SEQUENCE: 10

Arg Ala Ser Gln Ser Ile Ala Asn Tyr Leu Asn
1               5                   10

<210> SEQ ID NO 11
<211> LENGTH: 7
<212> TYPE: PRT
<213> ORGANISM: Artificial
<220> FEATURE:
<223> OTHER INFORMATION: MSLN37 LCDR2

<400> SEQUENCE: 11

Ala Ala Ser Asn Leu Gln Ser
1               5

<210> SEQ ID NO 12
<211> LENGTH: 9
<212> TYPE: PRT
<213> ORGANISM: Artificial
<220> FEATURE:
<223> OTHER INFORMATION: MSLN37 LCDR3

<400> SEQUENCE: 12

Gln Gln Ser Tyr Ser Phe Pro Tyr Thr
1               5

<210> SEQ ID NO 13
<211> LENGTH: 5
<212> TYPE: PRT
<213> ORGANISM: Artificial
<220> FEATURE:
<223> OTHER INFORMATION: MSLN38 HCDR1

<400> SEQUENCE: 13

Ser Tyr Ala Met Ser
1               5
```

```
<210> SEQ ID NO 14
<211> LENGTH: 17
<212> TYPE: PRT
<213> ORGANISM: Artificial
<220> FEATURE:
<223> OTHER INFORMATION: MSLN38 HCDR2

<400> SEQUENCE: 14

Gly Ile Ser Gly Ser Gly Gly Ser Thr Gly Tyr Ala Asp Ser Val Lys
1               5                   10                  15

Gly

<210> SEQ ID NO 15
<211> LENGTH: 12
<212> TYPE: PRT
<213> ORGANISM: Artificial
<220> FEATURE:
<223> OTHER INFORMATION: MSLN38 HCDR3

<400> SEQUENCE: 15

His Gly Gln Val Gly Gly Ile Ser Val Phe Asp Ile
1               5                   10

<210> SEQ ID NO 16
<211> LENGTH: 11
<212> TYPE: PRT
<213> ORGANISM: Artificial
<220> FEATURE:
<223> OTHER INFORMATION: MSLN38 LCDR1

<400> SEQUENCE: 16

Arg Ala Ser Gln Ser Ile Ser Asn Trp Leu Asn
1               5                   10

<210> SEQ ID NO 17
<211> LENGTH: 7
<212> TYPE: PRT
<213> ORGANISM: Artificial
<220> FEATURE:
<223> OTHER INFORMATION: MSLN38 LCDR2

<400> SEQUENCE: 17

Ala Thr Ser Arg Leu Gln Ser
1               5

<210> SEQ ID NO 18
<211> LENGTH: 9
<212> TYPE: PRT
<213> ORGANISM: Artificial
<220> FEATURE:
<223> OTHER INFORMATION: MSLN38 LCDR3

<400> SEQUENCE: 18

Gln Gln Ser Tyr Ser Phe Pro Trp Thr
1               5

<210> SEQ ID NO 19
<211> LENGTH: 121
<212> TYPE: PRT
<213> ORGANISM: Artificial
<220> FEATURE:
<223> OTHER INFORMATION: MSLN34 VH

<400> SEQUENCE: 19

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
            35                  40                  45

Ser Ser Ile Tyr Gly Ser Gly Gly His Thr Gly Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln His Ala Tyr Arg Tyr Ser Tyr Ala Phe Asp Val Trp Gly
            100                 105                 110

Gln Gly Thr Leu Val Thr Val Ser Ser
            115                 120

<210> SEQ ID NO 20
<211> LENGTH: 107
<212> TYPE: PRT
<213> ORGANISM: Artificial
<220> FEATURE:
<223> OTHER INFORMATION: MSLN34 VL

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Trp
            20                  25                  30

Leu Asn Trp Tyr Gln Gln Lys Pro Gly Lys Ala Pro Lys Leu Leu Ile
            35                  40                  45

Tyr Ala Thr Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Phe
                85                  90                  95

Thr Phe Gly Gln Gly Thr Lys Val Glu Ile Lys
            100                 105

<210> SEQ ID NO 21
<211> LENGTH: 121
<212> TYPE: PRT
<213> ORGANISM: Artificial
<220> FEATURE:
<223> OTHER INFORMATION: MSLN37 VH

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ser Gly Ile Ser Gly Ser Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Glu Val Glu Gly Gln Ser Gln Glu Tyr Phe Asp Ile Trp Gly
            100                 105                 110

Gln Gly Thr Leu Val Thr Val Ser Ser
        115                 120
```

<210> SEQ ID NO 22
<211> LENGTH: 107
<212> TYPE: PRT
<213> ORGANISM: Artificial
<220> FEATURE:
<223> OTHER INFORMATION: MSLN37 VL

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Tyr
                85                  90                  95

Thr Phe Gly Gln Gly Thr Lys Val Glu Ile Lys
            100                 105
```

<210> SEQ ID NO 23
<211> LENGTH: 121
<212> TYPE: PRT
<213> ORGANISM: Artificial
<220> FEATURE:
<223> OTHER INFORMATION: MSLN38 VH

<400> SEQUENCE: 23

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Gln Val Gly Gly Ile Ser Val Phe Asp Ile Trp Gly
            100                 105                 110

Gln Gly Thr Leu Val Thr Val Ser Ser
        115                 120
```

<210> SEQ ID NO 24
<211> LENGTH: 107
<212> TYPE: PRT
<213> ORGANISM: Artificial
<220> FEATURE:
<223> OTHER INFORMATION: MSLN38 VL

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Trp
            20                  25                  30

Leu Asn Trp Tyr Gln Gln Lys Pro Gly Lys Ala Pro Lys Leu Leu Ile
        35                  40                  45

Tyr Ala Thr Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys
            100                 105

<210> SEQ ID NO 25
<211> LENGTH: 63
<212> TYPE: DNA
<213> ORGANISM: Artificial
<220> FEATURE:
<223> OTHER INFORMATION: CD8

<400> SEQUENCE: 25
atggccttac cagtgaccgc cttgctcctg ccgctggcct tgctgctcca cgccgccagg      60
ccg                                                                   63

<210> SEQ ID NO 26
<211> LENGTH: 738
<212> TYPE: DNA
<213> ORGANISM: Artificial
<220> FEATURE:
<223> OTHER INFORMATION: MSLN34 scFv

<400> SEQUENCE: 26
gaagtacagt tggtcgaaag tggcggtggc ctcgtgcaac cgggtggttc actgcgtctg      60
agctgcgccg cctcgggttt tactttctct gattatggta tgcactgggt tcgtcaggcg     120
ccgggcaagg gtctcgaatg ggtttcatct atctacggtt ctggtggtca cactggttat     180
gccgattcag tgaagggtcg ctttaccatt tcccgtgaca actctaagaa tactctgtat     240
ctgcagatga actcgctgcg tgccgaagac acggccgtct attattgcgc caaacagcat     300
gcataccgtt actcttacgc attcgatgtt tggggtcagg gcactttagt gaccgtctca     360
tcgggtggag gcggttcagg cggaggtgga tccggcggtg gcggatcgga cattcaaatg     420
acgcagagtc cctcctcact gagtgctagc gtgggcgatc gtgtgacaat tacttgtcgc     480
gctagccagt ctatctctaa ttggctgaac tggtatcagc agaaaccggg caaggcgcca     540
aaattgctga tttacgcaac ttcctctctg cagtctggtg taccgtcccg tttctctggc     600
agcggttctg gtacggattt taccctgacc atctcaagcc tccagcctga agattttgcc     660
acctattatt gtcagcaatc ttactctttt ccgtttacgt tcgggcaggg aactaaagtg     720
gaaattaaag ccagcacc                                                   738

<210> SEQ ID NO 27
<211> LENGTH: 738
<212> TYPE: DNA
<213> ORGANISM: Artificial

```
<220> FEATURE:
<223> OTHER INFORMATION: MSLN38 scFv

<400> SEQUENCE: 27
gaagtacagt tggtcgaaag tggcggtggc ctcgtgcaac cgggtggttc actgcgtctg      60
agctgcgccg cctcgggttt tactttctct tcttatgcaa tgtcttgggt tcgtcaggcg     120
ccgggcaagg gtctcgaatg ggtttcaggt atctctggtt ctggtggttc tactggttat     180
gccgattcag tgaagggtcg ctttaccatt tcccgtgaca actctaagaa tactctgtat     240
ctgcagatga actcgctgcg tgccgaagac acggccgtct attattgcgc caaacatggt     300
caggttggtg gtatctctgt tttcgatatc tggggtcagg gcactttagt gaccgtctca     360
tcgggtggag gcggttcagg cggaggtgga tccggcggtg gcggatcgga cattcaaatg     420
acgcagagtc cctcctcact gagtgctagc gtgggcgatc gtgtgacaat tacttgtcgc     480
gctagccagt ctatctctaa ttggctgaac tggtatcagc agaaaccggg caaggcgcca     540
aaattgctga tttacgcaac ttcccgtctg cagtctggtg taccgtcccg tttctctggc     600
agcggttctg gtacggattt taccctgacc atctcaagcc tccagcctga agattttgcc     660
acctattatt gtcagcaatc ttactctttt ccgtggacgt tcgggcaggg aactaaagtg     720
gaaattaaag ccagcacc                                                   738

<210> SEQ ID NO 28
<211> LENGTH: 135
<212> TYPE: DNA
<213> ORGANISM: Artificial
<220> FEATURE:
<223> OTHER INFORMATION: CD8 hinge

<400> SEQUENCE: 28
accacgacgc cagcgccgcg accaccaaca ccggcgccca ccatcgcgtc gcagccctg       60 tccctgcgcc cagaggcgtg ccggccagcg gcggggggcg cagtgcacac gagggggctg    120
gacttcgcct gtgat                                                     135

<210> SEQ ID NO 29
<211> LENGTH: 72
<212> TYPE: DNA
<213> ORGANISM: Artificial
<220> FEATURE:
<223> OTHER INFORMATION: CD8 TM(TransMembrane)

<400> SEQUENCE: 29
atctacatct gggcgcccttt ggccgggact tgtgggtgtcc ttctcctgtc actggttatc      60 acccttact gc                                                         72

<210> SEQ ID NO 30
<211> LENGTH: 126
<212> TYPE: DNA
<213> ORGANISM: Artificial
<220> FEATURE:
<223> OTHER INFORMATION: 4-1BB

<400> SEQUENCE: 30
aaacggggca gaagaaact cctgtatata ttcaaacaac catttatgag accagtacaa      60
actactcaag aggaagatgg ctgtagctgc cgatttccag aagaagaaga aggaggatgt    120
gaactg                                                               126

<210> SEQ ID NO 31
```

<210> SEQ ID NO 31
<211> LENGTH: 337
<212> TYPE: DNA
<213> ORGANISM: Artificial
<220> FEATURE:
<223> OTHER INFORMATION: CD3z

<400> SEQUENCE: 31

```
agagtgaagt tcagcaggag cgcagacgcc ccgcgtaca cagcagggcc agaaccagct      60
ctataacgag ctcaatctag gacgaagaga ggagtacgat gttttggaca agagacgtgg    120
ccgggaccct gagatggggg gaaagccgag aaggaagaac cctcaggaag gcctgtacaa    180
tgaactgcag aaagataaga tggcggaggc ctacagtgag attgggatga aggcgagcg     240
ccggaggggc aagggggcacg atggccttta ccagggtctc agtacagcca ccaaggacac    300
ctacgacgcc cttcacatgc aggccctgcc ccctcgc                              337
```

<210> SEQ ID NO 32
<211> LENGTH: 5
<212> TYPE: PRT
<213> ORGANISM: Artificial
<220> FEATURE:
<223> OTHER INFORMATION: MSLN3 HCDR1

<400> SEQUENCE: 32

Asp Tyr Ala Met Ser
1               5

<210> SEQ ID NO 33
<211> LENGTH: 17
<212> TYPE: PRT
<213> ORGANISM: Artificial
<220> FEATURE:
<223> OTHER INFORMATION: MSLN3 HCDR2

<400> SEQUENCE: 33

Ala Ile Ser Ser Ser Gly Gly Thr Thr Tyr Tyr Ala Asp Ser Val Lys
1               5                   10                  15

Gly

<210> SEQ ID NO 34
<211> LENGTH: 12
<212> TYPE: PRT
<213> ORGANISM: Artificial
<220> FEATURE:
<223> OTHER INFORMATION: MSLN3 HCDR3

<400> SEQUENCE: 34

Glu Glu Glu Gly Glu Trp Arg Glu Tyr Phe Asp Val
1               5                   10

<210> SEQ ID NO 35
<211> LENGTH: 11
<212> TYPE: PRT
<213> ORGANISM: Artificial
<220> FEATURE:
<223> OTHER INFORMATION: MSLN3 LCDR1

<400> SEQUENCE: 35

Arg Ala Ser Gln Ser Ile Ser Ser Tyr Leu Asn
1               5                   10

<210> SEQ ID NO 36
<211> LENGTH: 7
<212> TYPE: PRT
<213> ORGANISM: Artificial

```
<220> FEATURE:
<223> OTHER INFORMATION: MSLN3 LCDR2

<400> SEQUENCE: 36

Ala Thr Ser Thr Leu Gln Ser
1               5

<210> SEQ ID NO 37
<211> LENGTH: 9
<212> TYPE: PRT
<213> ORGANISM: Artificial
<220> FEATURE:
<223> OTHER INFORMATION: MSLN3 LCDR3

<400> SEQUENCE: 37

Gln Gln Ser Tyr Thr Phe Pro Tyr Thr
1               5

<210> SEQ ID NO 38
<211> LENGTH: 121
<212> TYPE: PRT
<213> ORGANISM: Artificial
<220> FEATURE:
<223> OTHER INFORMATION: MSLN3 VH

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ala Ile Ser Ser Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Glu Glu Gly Glu Trp Arg Glu Tyr Phe Asp Val Trp Gly
            100                 105                 110

Gln Gly Thr Leu Val Thr Val Ser Ser
        115                 120

<210> SEQ ID NO 39
<211> LENGTH: 107
<212> TYPE: PRT
<213> ORGANISM: Artificial
<220> FEATURE:
<223> OTHER INFORMATION: MSLN3 VL

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Thr Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Tyr Thr Phe Pro Tyr
                85                  90                  95

Thr Phe Gly Gln Gly Thr Lys Val Glu Ile Lys
            100                 105

<210> SEQ ID NO 40
<211> LENGTH: 630
<212> TYPE: PRT
<213> ORGANISM: Artificial
<220> FEATURE:
<223> OTHER INFORMATION: MSLN(mesothelin)

<400> SEQUENCE: 40

Met Ala Leu Pro Thr Ala Arg Pro Leu Leu Gly Ser Cys Gly Thr Pro
1               5                   10                  15

Ala Leu Gly Ser Leu Leu Phe Leu Phe Ser Leu Gly Trp Val Gln
                20                  25                  30

Pro Ser Arg Thr Leu Ala Gly Glu Thr Gly Gln Glu Ala Ala Pro Leu
            35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335
```

```
Asp Arg Val Asn Ala Ile Pro Phe Thr Tyr Glu Gln Leu Asp Val Leu
            340             345             350

Lys His Lys Leu Asp Glu Leu Tyr Pro Gln Gly Tyr Pro Glu Ser Val
        355             360             365

Ile Gln His Leu Gly Tyr Leu Phe Leu Lys Met Ser Pro Glu Asp Ile
    370             375             380

Arg Lys Trp Asn Val Thr Ser Leu Glu Thr Leu Lys Ala Leu Leu Glu
385             390             395             400

Val Asn Lys Gly His Glu Met Ser Pro Gln Ala Pro Arg Arg Pro Leu
            405             410             415

Pro Gln Val Ala Thr Leu Ile Asp Arg Phe Val Lys Gly Arg Gly Gln
            420             425             430

Leu Asp Lys Asp Thr Leu Asp Thr Leu Thr Ala Phe Tyr Pro Gly Tyr
            435             440             445

Leu Cys Ser Leu Ser Pro Glu Glu Leu Ser Ser Val Pro Pro Ser Ser
            450             455             460

Ile Trp Ala Val Arg Pro Gln Asp Leu Asp Thr Cys Asp Pro Arg Gln
465             470             475             480

Leu Asp Val Leu Tyr Pro Lys Ala Arg Leu Ala Phe Gln Asn Met Asn
                485             490             495

Gly Ser Glu Tyr Phe Val Lys Ile Gln Ser Phe Leu Gly Gly Ala Pro
            500             505             510

Thr Glu Asp Leu Lys Ala Leu Ser Gln Gln Asn Val Ser Met Asp Leu
            515             520             525

Ala Thr Phe Met Lys Leu Arg Thr Asp Ala Val Leu Pro Leu Thr Val
        530             535             540

Ala Glu Val Gln Lys Leu Leu Gly Pro His Val Glu Gly Leu Lys Ala
545             550             555             560

Glu Glu Arg His Arg Pro Val Arg Asp Trp Ile Leu Arg Gln Arg Gln
            565             570             575

Asp Asp Leu Asp Thr Leu Gly Leu Gly Leu Gln Gly Gly Ile Pro Asn
            580             585             590

Gly Tyr Leu Val Leu Asp Leu Ser Met Gln Glu Ala Leu Ser Gly Thr
        595             600             605

Pro Cys Leu Leu Gly Pro Gly Pro Val Leu Thr Val Leu Ala Leu Leu
        610             615             620

Leu Ala Ser Thr Leu Ala
625             630
```